United States Patent
Firlik et al.

(10) Patent No.: US 8,706,241 B2
(45) Date of Patent: Apr. 22, 2014

(54) SYSTEM FOR PATENT INTERACTIVE NEURAL STIMULATION WITH ROBOTIC FACILITATION OF LIMB MOVEMENT

(75) Inventors: Andrew D Firlik, New Canaan, CT (US); Bradford Evan Gliner, Sammamish, WA (US); W Douglas Sheffirld, Seattle, WA (US); Leif R Sloan, Seattle, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 792 days.

(21) Appl. No.: 12/973,471

(22) Filed: Dec. 20, 2010

(65) Prior Publication Data

US 2011/0092882 A1 Apr. 21, 2011

Related U.S. Application Data

(63) Continuation of application No. 11/255,187, filed on Oct. 19, 2005, now Pat. No. 7,856,264.

(51) Int. Cl.
*A61N 1/36* (2006.01)
*G06F 19/00* (2011.01)
*A61F 2/70* (2006.01)

(52) U.S. Cl.
CPC ........ *A61N 1/36067* (2013.01); *A61N 1/36139* (2013.01); *G06F 19/3481* (2013.01); *A61F 2002/704* (2013.01); *A61N 1/36103* (2013.01)
USPC .................................. 607/48; 607/3; 607/62

(58) Field of Classification Search
None
See application file for complete search history.

(56) References Cited

U.S. PATENT DOCUMENTS

| | | | |
|---|---|---|---|
| 2,721,316 | A | 10/1955 | Shaw |
| 3,628,193 | A | 12/1971 | Collins |
| 3,650,276 | A | 3/1972 | Burghele et al. |
| 4,140,133 | A | 2/1979 | Kastrubin et al. |
| 4,214,804 | A | 7/1980 | Little |
| 4,431,000 | A | 2/1984 | Butler et al. |
| 4,474,186 | A | 10/1984 | Ledley et al. |

(Continued)

FOREIGN PATENT DOCUMENTS

| | | |
|---|---|---|
| DE | 19750043 | 5/1999 |
| EP | 0998958 | 5/2000 |

(Continued)

OTHER PUBLICATIONS

Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).

(Continued)

*Primary Examiner* — Kennedy Schaetzle

(57) ABSTRACT

Systems and methods for patient interactive neural stimulation and/or chemical substance delivery are disclosed. A method in accordance with one embodiment of the invention includes affecting a target neural population of the patient by providing to the patient at least one of an electromagnetic signal and a chemical substance. The method can further include detecting at least one characteristic of the patient, with the characteristic at least correlated with the patient's performance of an adjunctive therapy task that is performed in association with affecting the target neural population. The method can still further include controlling at least one parameter in accordance with which the target neural population is affected, based at least in part on the detected characteristic.

14 Claims, 15 Drawing Sheets

(56) References Cited

U.S. PATENT DOCUMENTS

| | | |
|---|---|---|
| 4,542,752 A | 9/1985 | Dehaan et al. |
| 4,590,946 A | 5/1986 | Loeb |
| 4,607,639 A | 8/1986 | Tanagho et al. |
| 4,646,744 A | 3/1987 | Capel |
| 4,724,842 A * | 2/1988 | Charters .................. 607/48 |
| 4,844,075 A | 7/1989 | Liss et al. |
| 4,865,048 A | 9/1989 | Eckerson |
| 5,002,053 A | 3/1991 | Garcia-Rill et al. |
| 5,024,226 A | 6/1991 | Tan |
| 5,031,618 A | 7/1991 | Mullett |
| 5,054,906 A | 10/1991 | Lyons |
| 5,092,835 A | 3/1992 | Schurig et al. |
| 5,121,754 A | 6/1992 | Mullett |
| 5,143,089 A | 9/1992 | Alt |
| 5,169,384 A | 12/1992 | Bosniak et al. |
| 5,215,086 A | 6/1993 | Terry, Jr. et al. |
| 5,224,491 A | 7/1993 | Mehra |
| 5,255,678 A | 10/1993 | Deslauriers et al. |
| 5,263,967 A | 11/1993 | Lyons, III et al. |
| 5,282,468 A | 2/1994 | Klepinski |
| 5,299,569 A | 4/1994 | Wernicke et al. |
| 5,304,206 A | 4/1994 | Baker, Jr. et al. |
| 5,314,458 A | 5/1994 | Najafi et al. |
| 5,358,513 A | 10/1994 | Powell, III et al. |
| 5,370,672 A | 12/1994 | Fowler et al. |
| 5,406,957 A | 4/1995 | Tansey |
| 5,411,540 A | 5/1995 | Edell et al. |
| 5,417,719 A | 5/1995 | Hull et al. |
| 5,423,864 A | 6/1995 | Ljungstroem |
| 5,520,190 A | 5/1996 | Benedict et al. |
| 5,522,864 A | 6/1996 | Wallace et al. |
| 5,537,512 A | 7/1996 | Hsia et al. |
| 5,540,736 A | 7/1996 | Haimovich et al. |
| 5,549,655 A | 8/1996 | Erickson |
| 5,575,813 A | 11/1996 | Edell et al. |
| 5,591,216 A | 1/1997 | Testerman et al. |
| 5,593,432 A | 1/1997 | Crowther et al. |
| 5,601,611 A | 2/1997 | Fayram et al. |
| 5,628,317 A | 5/1997 | Starkebaum et al. |
| 5,674,251 A | 10/1997 | Combs et al. |
| 5,683,422 A | 11/1997 | Rise |
| 5,702,429 A | 12/1997 | King |
| 5,711,316 A | 1/1998 | Elsberry et al. |
| 5,713,922 A | 2/1998 | King |
| 5,713,923 A | 2/1998 | Ward et al. |
| 5,716,377 A | 2/1998 | Rise et al. |
| 5,722,401 A | 3/1998 | Pietroski |
| 5,735,814 A | 4/1998 | Elsberry et al. |
| 5,752,979 A | 5/1998 | Benabid |
| 5,772,591 A | 6/1998 | Cram |
| 5,782,798 A | 7/1998 | Rise |
| 5,792,186 A | 8/1998 | Rise |
| 5,797,970 A | 8/1998 | Pouvreau |
| 5,814,014 A | 9/1998 | Elsberry et al. |
| 5,814,092 A | 9/1998 | King |
| 5,824,021 A | 10/1998 | Rise |
| 5,824,030 A | 10/1998 | Yang et al. |
| 5,832,932 A | 11/1998 | Elsberry et al. |
| 5,833,709 A | 11/1998 | Rise et al. |
| 5,843,148 A | 12/1998 | Gijsbers et al. |
| 5,843,150 A | 12/1998 | Dreessen et al. |
| 5,885,976 A | 3/1999 | Sandyk |
| 5,886,769 A | 3/1999 | Zolten |
| 5,893,883 A | 4/1999 | Torgerson et al. |
| 5,904,916 A | 5/1999 | Hirsch |
| 5,913,882 A | 6/1999 | King |
| 5,925,070 A | 7/1999 | King et al. |
| 5,938,688 A | 8/1999 | Schiff |
| 5,938,689 A | 8/1999 | Fischell et al. |
| 5,941,906 A | 8/1999 | Barreras, Sr. et al. |
| 5,964,794 A | 10/1999 | Bolz et al. |
| 5,975,085 A | 11/1999 | Rise |
| 5,978,702 A | 11/1999 | Ward et al. |
| 5,983,140 A | 11/1999 | Smith et al. |
| 6,006,124 A | 12/1999 | Fischell et al. |
| 6,011,996 A | 1/2000 | Gielen et al. |
| 6,016,449 A | 1/2000 | Fischell et al. |
| 6,018,682 A | 1/2000 | Rise |
| 6,021,352 A | 2/2000 | Christopherson et al. |
| 6,026,326 A | 2/2000 | Bardy |
| 6,035,236 A | 3/2000 | Jarding et al. |
| 6,042,579 A | 3/2000 | Elsberry et al. |
| 6,052,624 A | 4/2000 | Mann |
| 6,055,456 A | 4/2000 | Gerber |
| 6,057,847 A | 5/2000 | Jenkins |
| 6,058,331 A | 5/2000 | King |
| 6,060,048 A | 5/2000 | Cherksey |
| 6,061,593 A | 5/2000 | Fischell et al. |
| 6,066,163 A | 5/2000 | John |
| 6,104,956 A | 8/2000 | Naritoku et al. |
| 6,104,960 A | 8/2000 | Duysens et al. |
| 6,122,548 A | 9/2000 | Starkebaum et al. |
| 6,126,657 A | 10/2000 | Edwards et al. |
| 6,128,537 A | 10/2000 | Rise |
| 6,128,538 A | 10/2000 | Fischell et al. |
| 6,134,474 A | 10/2000 | Fischell et al. |
| 6,152,143 A | 11/2000 | Edwards |
| 6,161,044 A | 12/2000 | Silverstone |
| 6,161,045 A | 12/2000 | Fischell et al. |
| 6,198,958 B1 | 3/2001 | Ives et al. |
| 6,205,360 B1 | 3/2001 | Carter et al. |
| 6,221,908 B1 | 4/2001 | Kilgard et al. |
| 6,230,049 B1 | 5/2001 | Fischell et al. |
| 6,236,892 B1 | 5/2001 | Feler |
| 6,280,462 B1 | 8/2001 | Hauser et al. |
| 6,301,493 B1 | 10/2001 | Marro et al. |
| 6,339,725 B1 | 1/2002 | Naritoku et al. |
| 6,353,754 B1 | 3/2002 | Fischell et al. |
| 6,354,299 B1 | 3/2002 | Fischell et al. |
| 6,360,122 B1 | 3/2002 | Fischell et al. |
| 6,366,813 B1 | 4/2002 | DiLorenzo |
| 6,375,666 B1 | 4/2002 | Mische |
| 6,405,079 B1 | 6/2002 | Ansarinia |
| 6,418,344 B1 | 7/2002 | Rezai |
| 6,427,086 B1 | 7/2002 | Fischell et al. |
| 6,459,936 B2 | 10/2002 | Fischell et al. |
| 6,463,328 B1 | 10/2002 | John |
| 6,464,356 B1 | 10/2002 | Sabel et al. |
| 6,466,822 B1 | 10/2002 | Pless |
| 6,473,639 B1 | 10/2002 | Fischell et al. |
| 6,480,743 B1 | 11/2002 | Kirkpatrick et al. |
| 6,484,059 B2 | 11/2002 | Gielen |
| 6,487,450 B1 | 11/2002 | Chen |
| 6,499,488 B1 | 12/2002 | Hunter et al. |
| 6,505,075 B1 | 1/2003 | Weiner |
| 6,507,755 B1 | 1/2003 | Gozani et al. |
| 6,597,954 B1 | 7/2003 | Pless et al. |
| 6,615,065 B1 | 9/2003 | Barrett et al. |
| 6,622,048 B1 | 9/2003 | Mann et al. |
| 6,633,780 B1 | 10/2003 | Berger |
| 6,665,562 B2 | 12/2003 | Gluckman et al. |
| 6,687,525 B2 | 2/2004 | Llinas et al. |
| 6,690,974 B2 | 2/2004 | Archer et al. |
| 6,725,094 B2 | 4/2004 | Saberski |
| 6,764,498 B2 | 7/2004 | Mische |
| 6,782,292 B2 | 8/2004 | Whitehurst |
| 6,795,737 B2 | 9/2004 | Gielen et al. |
| 6,810,286 B2 | 10/2004 | Donovan et al. |
| 6,819,956 B2 | 11/2004 | DiLorenzo |
| 6,839,594 B2 | 1/2005 | Cohen et al. |
| 6,873,872 B2 | 3/2005 | Gluckman et al. |
| 6,892,097 B2 | 5/2005 | Holsheimer |
| 6,907,296 B1 | 6/2005 | Doan et al. |
| 6,934,580 B1 | 8/2005 | Osorio et al. |
| 6,944,497 B2 | 9/2005 | Stypulkowski |
| 6,949,081 B1 | 9/2005 | Chance |
| 6,959,215 B2 | 10/2005 | Gliner et al. |
| 2002/0087201 A1 | 7/2002 | Firlik et al. |
| 2002/0091419 A1 | 7/2002 | Firlik |
| 2002/0099412 A1 | 7/2002 | Fischell et al. |
| 2002/0169485 A1 | 11/2002 | Pless et al. |
| 2003/0125772 A1 | 7/2003 | Olson et al. |
| 2003/0125786 A1 | 7/2003 | Gliner et al. |
| 2003/0130706 A1 | 7/2003 | Sheffield et al. |

(56) References Cited

U.S. PATENT DOCUMENTS

| | | | |
|---|---|---|---|
| 2003/0149457 A1 | 8/2003 | Tcheng et al. | |
| 2003/0176901 A1 | 9/2003 | May | |
| 2003/0187490 A1 | 10/2003 | Gliner | |
| 2003/0187491 A1 | 10/2003 | Greenberg et al. | |
| 2004/0090333 A1 | 5/2004 | Wildman et al. | |
| 2004/0092809 A1 | 5/2004 | DeCharms | |
| 2004/0138550 A1 | 7/2004 | Hartlep et al. | |
| 2004/0158298 A1 | 8/2004 | Gliner et al. | |
| 2004/0176831 A1 | 9/2004 | Gliner et al. | |
| 2004/0236388 A1 | 11/2004 | Gielen et al. | |
| 2004/0243205 A1 | 12/2004 | Keravel et al. | |
| 2005/0004620 A1 | 1/2005 | Singhal et al. | |
| 2005/0015129 A1 | 1/2005 | Mische | |
| 2005/0055069 A1 | 3/2005 | Franck | |
| 2005/0090756 A1 | 4/2005 | Wolf et al. | |
| 2005/0096701 A1 | 5/2005 | Donovan et al. | |
| 2005/0113882 A1 | 5/2005 | Cameron et al. | |
| 2005/0119712 A1 | 6/2005 | Shafer | |
| 2005/0154425 A1 | 7/2005 | Boveja et al. | |
| 2005/0154426 A1 | 7/2005 | Boveja et al. | |
| 2007/0265489 A1 | 11/2007 | Fowler et al. | |
| 2008/0208284 A1* | 8/2008 | Rezai et al. | 607/45 |
| 2008/0234781 A1* | 9/2008 | Einav et al. | 607/48 |
| 2009/0221928 A1* | 9/2009 | Einav et al. | 600/544 |
| 2010/0198115 A1* | 8/2010 | Koeneman et al. | 601/5 |

FOREIGN PATENT DOCUMENTS

| | | |
|---|---|---|
| EP | 1145736 | 10/2001 |
| EP | 1180056 | 11/2003 |
| WO | WO 87-07511 | 12/1987 |
| WO | WO 94-07564 | 4/1994 |
| WO | WO 95-21591 | 8/1995 |
| WO | WO 98-06342 | 2/1998 |
| WO | WO 01-97906 | 12/2001 |
| WO | WO 02-09811 | 2/2002 |
| WO | WO 02-36003 | 5/2002 |
| WO | WO 02-38031 | 5/2002 |
| WO | WO 02-38217 | 5/2002 |
| WO | WO 03-000161 | 1/2003 |
| WO | WO 03-043690 | 5/2003 |
| WO | WO 03-082402 | 10/2003 |
| WO | WO 2005-061045 | 7/2005 |
| WO | WO 2006-063457 | 6/2006 |

OTHER PUBLICATIONS

Behrens, T. et al., "Non-invasive mapping of connections between human thalamus and cortex using diffusion imaging," Nature neuroscience, vol. 6 No. 7, pp. 750-757 (Jul. 2003).
Bel, S. and Bauer, B.L., "Dorsal Column Stimulation (DCS): Cost to Benefit Analysis," Acta Neurochirurgica, Suppl. 52, pp. 121-123 (1991).
Benabid, A.L. et al., "Chronic electrical stimulation of the ventralis intemedius nucleus of the thalamus as a treatment of movement disorders," J. Neurosurg., Apr. 1997, 86(4); 737; http:--www.ncbi.nlm.nih.gov; [accessed Nov. 18, 2003].
Brain Electrical Stimulation to Enhance Recovery After Stroke, ClinicalTrials.gov, URL: http://www.clinicaltrials.gov/ct/show/NCT00085657?order=2 [Retrieved on Dec. 22, 2005].
Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).
Butefisch et al., "Mechanisms of use-dependent plasticity in the human motor cortex," Proc. Natl. Acad. Sci. USA, vol. 97, No. 7, pp. 3661-3665 (Mar. 2000).
Canavero, S. and Paolotti, R., "Extradural Motor Cortex Stimulation for Advanced Parkinson's Disease: Case Report," Movement Disorders, Jan. 2000, 15(1):169-171.
Cincotta et al., "Reorganization of the motor cortex in a patient with congenital hemiparesis and mirror movements," Neurology, Jul. 12, 2000, 5+A535(1), pp. 129-131.
Classen et al., "Rapid Plasticity of Human Cortical Movement Representation Induced by Practice," The Journal of Neurophysiology, vol. 79, No. 2, pp. 1117-1123 (Feb. 1998).
Cohen et al., "Studies of Neuroplasticity With Transcranial Magnetic Stimulation," The Journal of Clinical Neurophysiology, vol. 15, No. 4 (1998).
Cramer, S.C. and Bastings, E.P., "Mapping clinically relevant plasticity after stroke," Neuropharmacology vol. 19, No. 5, pp. 842-851 (Apr. 2000).
Cytokines Web Clinical Significance, Cytokines Web, 2 pages, URL: http:--cmbi.bjmu.edu.cn-cmbidata-cgf-CGF__Database-cytweb-roles-index.html [Retrieved on Sep. 2, 2005].
Dam et al., "Effects of Fluoxetine and Maprotiline on Functional Recovery in Poststroke Hemiplegic Patients Undergoing Rehabilitation Therapy," Stroke, vol. 27, No. 7, pp. 121-1214 (Jul. 1996).
De Ridder, Dirk et al., "Magnetic and electrical stimulation of the auditory cortex for intractable tinnitus," Journal Neurosurg., vol. 100, pp. 560-564, (Mar. 2004).
Di Lazzaro, V. et al., "Theta-burst repetitive transcranial magnetic stimulation suppresses specific excitatory circuits in the human motor cortex," Physiology in Press; published online on Apr. 21, 2005 as 10.1113-jphysiol.2005.087288.
Ding, Yuemin et al., "Neural Plasticity After Spinal Cord Injury," Current Pharmaceutical Design vol. 11, No. 11, pp. 1441-1450, Abstract Only, 1 page (Apr. 2005).
Duncan, Pamela W. et al., "Defining post-stroke recovery: implications for design and interpretation of drug trials," Neuropharmacology vol. 39, pp. 835-841 (2000).
Feys et al., "Value of somatosensory and motor evoked potentials in predicting arm recovery after a stroke," (Oct. 1999).
Franzini et al., "Reversal of thalamic hand syndrome by long-term motor cortex stimulation," Journal of Neurosurgery 93(5)873-875, Nov. 2000.
Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).
Gladstone et al., "Enhancing Recovery after Stroke with Noradrenergic Pharmacotherapy: A New Frontier?" Can J. Neural. Sci., vol. 27, No. 2, May 2000, pp. 97-105.
Gordon et al., "Parameters for direct cortical electrical stimulation in the human: histopathologic confirmation," Electroencephalography and clinical Neurophysiology, vol. 75, pp. 371-377 (1990).
Hagemann, Georg et al., "Increased Long-Term Potentiation in the Surround of Experimentally Induced Focal Cortical Infarction," Annals of Neurology, vol. 44, No. 2, pp. 255-258 (Aug. 1998).
Hayakawa, Toshiji et al., "Changes in Cerebral Oxygenation and Hemodynamics During Obstructive Sleep Apneas," Chest, vol. 109, pp. 916-921 (1996).
Hodge, Jr., C.J. and Boakye, M., "Biological Plasticity: The Future of Science in Neurosurgery," Neurosurgery, vol. 48, No. 1 (Jan. 2001).
Hoshi, Yoko et al., "Detection of dynamic changes in cerebral oxygenation coupled to neuronal function during mental work in a man," Neuroscience Letters, vol. 150, pp. 5-8 (1993).
Hoshino et al., "Application of multichannel near-infrared spectroscopic topography to physiological monitoring of the cortex during cortical mapping: technical case report," Surgical Neurology, vol. 64, pp. 272-275 (2005).
Huang, Ying-Zu et al., "Theta Burst Stimulation of the Human Motor Cortex," Neuron, vol. 45, pp. 201-206 (Jan. 20, 2005).
Hummel, Friedhelm et al., "Effects of non-invasive cortical stimulation on skilled motor function in chronic stroke," Brain Advance Access, pp. 1-10, (Jan. 5, 2005).
Kauhanen et al., "Domains and Determinants of Quality of Life After Stroke Caused by Brain Infarction," Arch. Phys. Med. Rehabil., vol. 81, pp. 1541-1546 (Dec. 2000).
Kilgard, Michael et al., "Cortical Map Reorganization Enabled by Nucleus Basalis Activity," Science, vol. 279 pp. 1714-1717 (Mar. 13, 1998).
Kopell et al., "The Continuing Evolution of Psychiatric Neurosurgery," CNS Spectrums, vol. 5, No. 10, pp. 20-31 (Oct. 2000).
Lang, Nicolas et al., "Preconditioning with Transcranial Direct Current Stimulation Sensitizes the Motor Cortex to Rapid-Rate

(56) References Cited

OTHER PUBLICATIONS

Transcranial Magnetic Stimulation and Controls the Direction of After-Effects," Biol Psychiatry 2004:56:634-639, 2004 Society of Biological Psychiatry.
Larson, John et al., "Reversal of LTP by theta frequency stimulation," Brain Research, 600: pp. 97-102 (1993).
Lazar, M. et al., "White Matter Tractography Using Diffusion Tensor Deflection," Human Brain Mapping, 18:306-321, (2003).
L-DOPA dyskinesias, BioChemistry of PD, http://www.mayo.edu-ldp-pd-info-dyskinesias.htm [Retrieved on Dec. 22, 2005].
Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).
Liepert et al., "Treatment-Induced Cortical Reorganization After Stroke in Humans," Stroke, Jun. 2000, 31(6):1210-1216.
Malenka, R.C. and Nicoll, R.A., "Long-Term Potenetiation—A Decade of Progress?," Neuroscience, vol. 285, No. 5435, Issue of Sep. 17, 1999, pp. 1870-1874.
Mansur, C.G. et al., "A sham stimulation-controlled trial of rTMS of the unaffected hemisphere in stroke patients," Neurology, vol. 64, pp. 1802-1804 (2005).
Martin et al., "Transcranial Magnetic Stimulation as a Complementary Treatment for Aphasia," Semin Speech Language, vol. 25, pp. 181-191 (2004) Abstract Only—1 page.
Martinez et al., "Motor hand recovery after stroke Prognostic yield of early transcranial magnetic stimulation," Electromyogr. Clin. Neurophysiol., Oct.-Dec. 1999, 39(7):405-410.
Meyerson, B.A. et al., "Motor Cortex Stimulation as Treatment of Trigeminal Neuropathic Pain", Acta Neurochirurgica Supplementum, vol. 58, pp. 150-153 (1993).
Netz et al,, "Reorganization of motor output in the non-affected hemisphere after stroke," Brain, 120, pp. 1579-1586 (1997).
Nitsche, M.A. and Paulus, W., "Excitability changes induced in the human motor cortex by weak transcranial direct current stimulation," The Journal of Physiology, Sep. 15, 2000, 527(3):1633-9.
Nitsche, Michael A. et al., "Facilitation of Implicit Motor Learning by Weak Transcranial Direct Current Stimulation of the Primary Cortex in the Human," Journal of Cognitive Neuroscience, May 2003, 15(4):619-26, Published by the MIT Press with the Cognitive Neuroscience Institute.
Nitsche, Michael A. et al., "Level of action of cathodal DC opographyn induced inhibition of the human motor cortex," Dec. 2, 2002, Clinical Neurophysiology 114 (2003) 600-604.
Oliveri et al., "Paired transcranial magnetic stimulation protocols reveal a pattern of inhibition and facilitation in the human parietal cortex," The Journal of Physiology, Dec. 1, 2000, 529.2, pp. 461-468.
Panchanathan, Sethuraman et al., "Rehabilitation of patients with hemispatial neglect using visual-haptic feedback in Virtual reality environment," http://www.public.asu.edu-~tmcdani-publications.htm, 5 pages [Retrieved on Dec. 22, 2005].
Pascual-Leone et al., "Study and Modulation of Human Cortical Excitability With Transcranial Magnetic Stimulation," Journal of Clinical Neurophysiology, Jul. 1998, 15(4):333-43, Published by Lippincott Williams & Wilkins.
Pascual-Leone et al., "Transcranial magnetic stimulation and neuroplasticity," Neuropshycholegia, Feb. 1999, 37(2):207-17.
Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.
Paulus, Walter, "Toward Establishing a Therapeutic Window for rTMS by Theta Burst Stimulation," Neuron, vol. 45, pp. 181-183 (Jan. 20, 2005).
Penn, Michael, "Stemming Parkinson's," On Wisconsin Alumni Magazine, Summer 2003, http://www.uwalumni.com-onwisconsin-2003_summer-research.html, 1 page [Retrieved on Dec. 22, 2005].
Rezai, "Neurostimulation," Neurological Research, vol. 22, No. 3 pp. 235-273 (Apr. 2000).
Rossi et al., "Effects of Repetitive Transcranial Magnetic Stimulation on Movement-related Cortical Activity in Humans," Cerebral Cortex, vol. 10, No. 8, pp. 802-808 (Aug. 2000).
Roux et al., "Chronic Motor Cortex Stimulation for Phantom Limb Pain: A Functional Magnetic Resonance Imagining Study: Technical Cast Report," Neurosurgery, vol. 48, No. 3 (Mar. 2001).
Saitou et al., "Cerebral Blood Volume and Oxygenation Among Poststroke Hemiplegic Patients: Effect of 13 Rehabilitation Tasks Measured by Near-Infrared Spectroscopy," Arch. Phys. Med. Rehabil., vol. 81 pp. 1348-1356 (Oct. 2000).
Sandkuhler, "Learning and memory in pain pathways," Pain, Nov. 2008, 88(2):113-18, Elsevier/North-Holland.
Sanes, "The Relation between Human Brain Activity and Hand Movements," NeuroImage, May 2000, 11(5), pp. 370-374.
Sanes, J. and Donoghue, J.P., "Plasticity and Primary Motor Cortex," Annual Review of Neuroscience, 2000, 23:393-415.
Schaefer, Pamela W. et al., "Assessing Tissue Viability with MR Diffusion and Perfusion Imaging," AJNR, 24: pp. 436-443 (Mar. 2003).
Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).
Schiff et al., "A neuromodulation strategy for rational therapy of complex brain injury states," Neurological Research, vol. 22 pp. 267-272 (Apr. 2000).
Schmidt, E M, et al., "Feasibility of a visual prosthesis for the blind based on intracortical microstimulation of the visual cortex," Brain, Oxford University Press, Oxford, GB, vol. 119, No. part 2, Apr. 1, 1996, pp. 507-522.
SCIRun, Scientific Computing and Imaging Institute. http://www.software.sci.utah.edu-scirun.html, 2 pages [Retrieved on Jul. 24, 2005].
Shimizu et al., "Therapeutic efficacy of transcranial magnetic stimulation for hereditary spinocerebellar degeneration," Tohoku Journal of Experimental Medicine, 189(3):203-11 (Nov. 1999).
Siebner et al., "Lasting cortical activation after repetitive TMS of the motor cortex," Neurology 54, pp. 956-963 (Feb. 2000).
Stefan et al., "Induction of plasticity in the human motor cortex by paired associative stimulation," Brain, vol. 123, No. 3, pp. 572-584 (Mar. 2000).
Strangman, Gary et al., "A Quantitative Comparison of Simultaneous BOLD fMRI and NIRS Recordings during Functional Brain Activation," NeuroImage, vol. 17, pp. 719-731 (2002).
Strangman, Gary et al., "Factors affecting the accuracy of near-infrared spectroscopy concentration calculations for focal changes in oxygenation parameters," NeuroImage, vol. 18, pp. 865-879 (2003).
Strangman, Gary et al., "Non-Invasive Neuroimaging Using Near-Infrared Light," Biological Psychiatry, vol. 52, pp. 679-693 (2002).
Strens, Lucy et al., "The Ipsilateral Human Motor Cortex Can Functionally Compensate for Acute Contralateral Motor Cortex Dysfunction," Current Biology, vol. 13, pp. 1201-1205 (Jul. 15, 2003).
Taga, Gentaro et al., "Brain imaging in awake infants by near-infrared optical topogrpahy," PNAS, vol. 100, No. 19, pp. 10722-10727 (Sep. 16, 2003).
The GES 250 for Dense-Array EEG Research, Electrical Geodesics, Inc., http://www.egi.com/ges250r_n.html, 3 pages [Retrieved on Aug. 25, 2005].
The INVOS Cerebral Oximeter, Somanetics, http://www.somanetics.net/invos.htm, 1 page [retrieved from the internet on Dec. 22, 2005].
Theoret, Hugo et al,, "Exploring Paradoxical Functional Facilitation with TMS," Supplements to Clinical Neurophysiology, vol. 56, pp. 211-219 (2003).
Thomas, Carmen et al., "Do Children with aggressive behavior have temporal lobe changes?" Alasbimn Journal, Year 5, No. 19, 8 pages (Jan. 2003).
Toronov, Vlad et al., "Near-infrared study of fluctuations in cerebral hemodynamics during rest and motor stimulation: Temporal analysis and spatial mapping," Medical Physics, vol. 27, No. 4, pp. 801-815 (Apr. 2000).

(56) References Cited

OTHER PUBLICATIONS

Tractography, Absolute Astronomy Reference, http://www.absoluteastronomy.com-encyclopedia-T-Tr-Tractography.htm, 2 pages [Retrieved on Jul. 24, 2005].

Tsubokawa, T. et al., "Chronic Motor Cortex Stimulation for the Treatment of Central Pain," Acta Neurochirurgica, Supplementum. vol. 52, pp. 137-139 (1991).

Tsubokawa, T. et al., "Chronic Motor Cortex Stimulation in Patients with Thalamic Pain," J. Neurosurg 78:393-401, (Mar. 1993).

Tsubokawa, T. et al., "Treatment of Thalamic Pain by Chronic Motor Cortex Stimulation", PACE, vol. 14, pp. 131-134 (Jan. 1991).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Turton et al., "Contralateral and ipsilateral EMG responses to transcranial magnetic stimulation during recovery of arm and hand function after stroke," Electroencephalography and Clinical Neurophysiology, Aug. 1996, 101(4):316-28, Elsevier.

Turton, A. and Lemon, R.N., "The contribution of fast corticospinal input to the voluntary activation of proximal muscles in normal subjects and in stroke patients," Exp. Brain Res., Dec. 1999, 129(4):559-572, Springer Berlin / Heidelberg.

Van Der Lee et al., "The Intra- and Interrater Reliability of the Action Research Arm Test, A Practical Test of Upper Extremity Function in Patients With Stroke," Arch. Phys. Med. Rehabil., vol. 82 pp. 14-19 (Jan. 2001).

Walker-Batson et al., "Amphetamine Paired With Physical Therapy Accelerates Motor Recovery After Stroke," Stroke, vol. 26, No. 12, pp. 2254-2259 (1995).

Weinand, Martin E. et al., "Cerebral blood flow and temporal lobe epileptogenicity," Retrieved from the Internet on Dec. 22, 2005, http://www.aans.org/education/journal/neurosurgical/nov96/1-5-3.asp, 13 pages.

Yokoh, Arika et al., "Intermittent versus continuous brain retraction," Journal of Neurosurgery, vol. 58, pp. 918-923 (Jun. 1983).

Ziemann et al., "Modulation of Plasticity in Human Motor Cortex after Forearm Ischernic Nerve Block," The Journal of Neuroscience 18(3):1115-1123 (Feb. 1998).

EPO, Supplementary Partial European Search Report for EP06838401 dated Oct. 14, 2009.

International Search Report for PCT/US2006/040908 dated Sep. 25, 2007.

\* cited by examiner

SYSTEM FOR PATENT INTERACTIVE NEURAL STIMULATION WITH ROBOTIC FACILITATION OF LIMB MOVEMENT

CROSS-REFERENCE TO RELATED APPLICATIONS

This application is a continuation of U.S. application Ser. No. 11/255,187, filed Oct. 19, 2005, now U.S. Pat. No. 7,856,264, which is incorporated herein by reference.

TECHNICAL FIELD

The present disclosure generally relates to neural stimulation and/or chemical substance delivery systems and methods in which automated or semi-automated subsystems, devices, and/or other elements facilitate patient performance of activities in association with neural stimulation and/or chemical substance therapies to increase the efficacy and/or efficiency associated with such therapies.

BACKGROUND

A wide variety of mental and physical processes are controlled or influenced by neural activity in particular regions of the brain. For example, the neural functions in some areas of the brain (i.e., the sensory or motor cortices) are organized according to physical or cognitive functions. In general, particular areas of the brain appear to have distinct functions in most individuals. In the majority of people, for example, the areas of the occipital lobes relate to vision, the regions of the left interior frontal lobes relate to language, and the regions of the cerebral cortex appear to be consistently involved with conscious awareness, memory, and intellect.

Many problems or abnormalities with body functions can be caused by dysfunction, damage, disease and/or disorders in the brain. Effectively treating such abnormalities may be very difficult. Epidemiological profiles indicate that the treatment and/or rehabilitation of neurologic dysfunction is extremely challenging due to patient population heterogeneity, for example, due to factors such as age, gender, ethnicity, cause, physiologic location, severity, and time since onset. For most patients exhibiting neurologic damage arising from, for example, a stroke, conventional treatments are not sufficient, and little can be done to significantly improve the function of an affected body part or cognitive function beyond the limited recovery that generally occurs naturally without intervention.

A stroke is a common condition that damages the brain. Strokes are generally caused by emboli (e.g., obstruction of a vessel), hemorrhages (e.g., rupture of a vessel), or thrombi (e.g., clotting) in the vascular system of a specific region of the brain, which in turn generally cause a loss or impairment of a neural function (e.g., neural functions related to facial muscles, limbs, speech, etc.). Stroke patients are typically treated using various forms of physical therapy to rehabilitate the loss of function of a limb or another affected body part. Stroke patients may also be treated using physical therapy plus drug treatment.

Certain types of electromechanical or robotic systems may enhance particular types of physical therapy rehabilitation activities. For example, interactive robotic devices may dynamically interface with patients to focus on motor skills by guiding the patient through a series of exercises. Known robotic assist devices targeting arm/hand rehabilitation provide a movable member for the patient to manipulate. The robotic rehabilitation devices may provide a patient with a series of movements to perform with mechanical assistance and/or resistance to aid in coordination and muscular development.

Functional Electrical Stimulation (FES) generally refers to systems and methods that apply electrical signals to peripheral nerves to restore partial or adequate function to particular muscles in the body that are otherwise paralyzed due to damaged or dysfunctional neural signaling pathways, e.g., due to spinal cord injury, stroke, disease, or other conditions. These conditions can break or otherwise disrupt the path or paths by which electrical signals generated by the brain normally travel to neuromuscular groups to effectuate coordinated muscle contraction patterns. As a result, even though the majority of nerves along a given signaling pathway may be intact, essentially no physiological signals are received from the spinal cord, and in turn the associated body parts do not function. FES systems and methods attempt to compensate for the disrupted, damaged, or dysfunctional physiological signaling pathways, and restore some function to the still intact muscles and nerves. Such systems and methods are known, e.g., to aid finger-grasp functions to muscles in the arm and hand; restore control to intra-cavity muscles, e.g., in the bladder or bowel; or enhance standing and/or gait function involving muscles in the hip and legs.

Although preexisting systems and methods may provide a certain level of benefit to individuals undergoing treatment and/or rehabilitation for neurologic dysfunction, such benefit is typically undesirably limited and many quality of life issues still remain. There is a need for systems and methods capable of providing more effective or sustained neurofunctional benefit.

DETAILED DESCRIPTION

Introduction

Figure 1A:
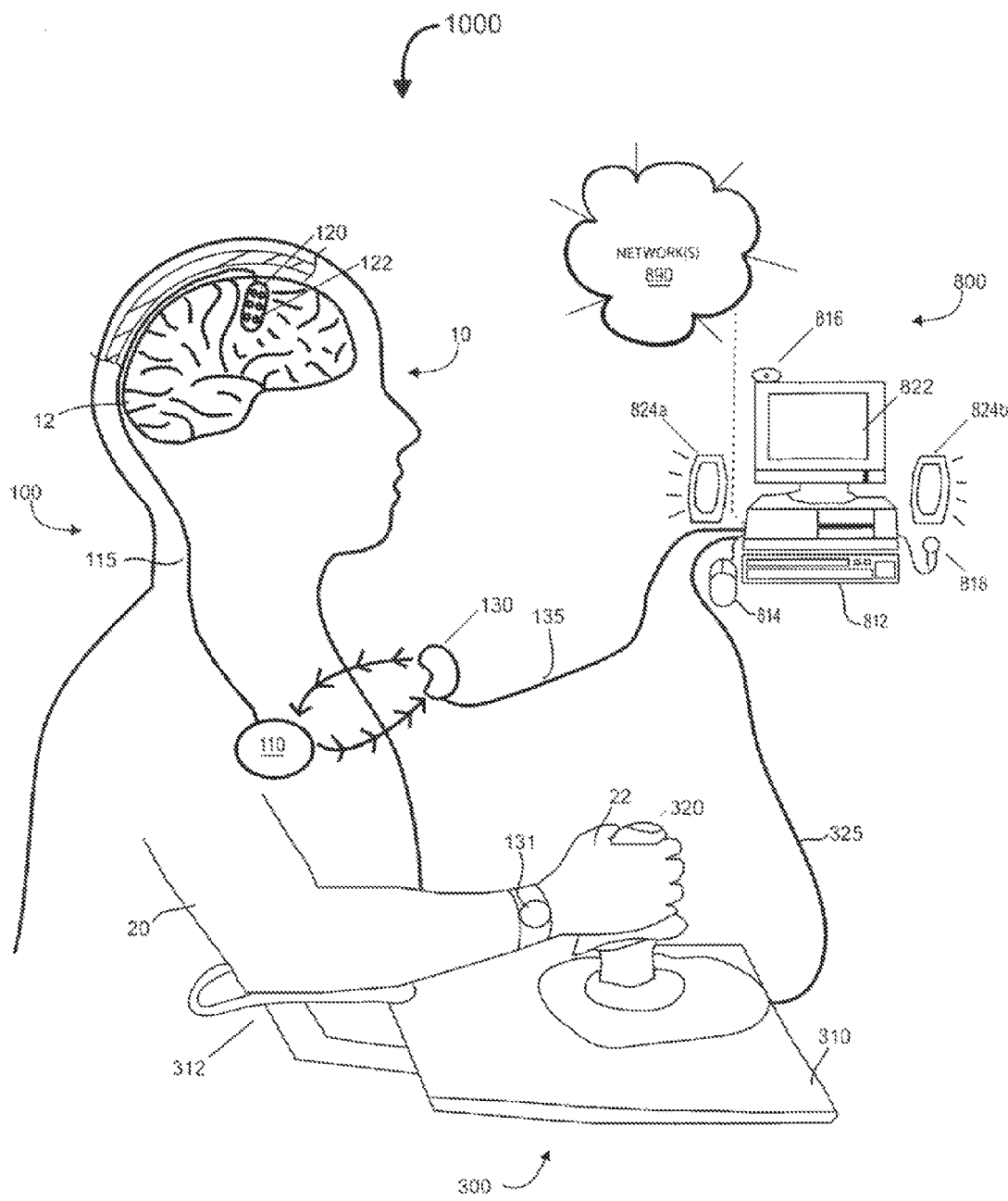
FIG. 1A is a schematic illustration of a patient interactive neural stimulation (PINS) system according to an embodiment of the invention according to an embodiment of the invention.

The following disclosure describes various embodiments of patient interactive neural therapy (PINT) systems and methods. Such systems and methods may be directed toward restoring, developing, and/or enhancing particular types of neural function, and/or treating or ameliorating neurologic dysfunction. Neurologic dysfunction may include disorders, diseases, injuries, and/or abnormalities related to brain and/or other neural tissue functions. Representative types of neurologic dysfunction may correspond to stroke, traumatic brain injury (TBI), a pain syndrome, auditory disorders (e.g., tinnitus or auditory hallucinations), speech or language disorders (e.g., aphasia), learning disorders (e.g., dyslexia), Parkinson's Disease, essential tremor, and/or one or more other disorders, states or conditions.

A method for treating a patient in accordance with a particular aspect of the invention includes affecting a target neural population of the patient by providing to the patient at least one of an electromagnetic signal and a chemical substance. The method can further include detecting at least one characteristic of the patient, with the characteristic being at least correlated with the patient's performance of an adjunctive therapy task. The adjunctive therapy task is performed in association with affecting the target neural population. The method can further include controlling at least one parameter in accordance with which the target neural population is affected, based at least in part on the detected characteristic.

In particular embodiments, detecting at least one characteristic of the patient can include detecting a manner in which the patient performs an adjunctive therapy task. For example, this process can include detecting a motion undertaken by the patient. In other embodiments, a physiologic characteristic of the patient (e.g., a patient heart rate or patient blood oxygenation characteristic) can be detected. The adjunctive therapy task can be performed at least approximately concurrently with the process of affecting the target neural population. For example, the patient can engage in a physical therapy task while receiving electrical stimulation of the patient's motor cortex. Controlling at least one parameter in accordance with which the target neural population is affected can include changing at least one parameter. For example, this process can include changing the waveform of an electrical signal applied to the patient.

Further aspects of the invention are directed to systems for treating a patient. One such system can include an adjunctive therapy device, a patient treatment delivery device that includes an electromagnetic stimulator and/or a chemical delivery device, and a control system operatively coupled to the adjunctive therapy device and the patient treatment device. The control system can include a computer-readable medium having instructions for automatically receiving information from the adjunctive therapy device, with the information being correlated with the patient's performance of a task at the adjunctive therapy device. The instructions can also automatically control a parameter in accordance with which the patient delivery device provides treatment to the patient, based at least in part on the information received from the adjunctive therapy device.

In particular embodiments, the adjunctive therapy device can include a patient-actuatable element and a feedback sensor. The feedback sensor can be coupled to the control system to direct to the control system at least one signal corresponding to the patient's manipulation of the actuatable element. The control system can control a parameter in accordance with which the patient treatment delivery device provides treatment to the patient in an at least approximately real-time manner relative to receiving information from the adjunctive therapy device.

In general, PINT systems and/or methods may be directed toward monitoring, controlling, managing, adjusting, and/or modifying one or more manners in which neural stimulation and/or chemical substance therapies may be provided to an individual in association with one or more behavioral activities or therapies to possibly influence, affect, maintain, or improve therapeutic efficacy and/or efficiency. In various embodiments, a PINT a system or method may involve 1) patient interactive neural stimulation (PINS); 2) patient interactive neural stimulation in association with one or more adjunctive chemical therapies (PINS-ACT); and/or 3) patient interactive chemical therapy (PICT), which may occur in association with one or more behavioral activities or therapies.

Depending upon embodiment details, particular PINT systems and/or methods may control, adjust, or modify one or more manners of delivering neural stimulation and/or chemical substances to a patient in an adaptive or nonadaptive manner. Particular adaptive or nonadaptive modifications may occur on a real time, near-real time basis, or delayed basis. Adaptive modifications may be based upon patient performance or progress in performing particular types of activities. Additionally or alternatively, adaptive or nonadaptive modifications may occur from or across 1) one or more sets of patient tasks or activities to one or more other task sets; 2) one treatment session to another; and/or 3) one time period (e.g., a number of days, weeks, or months) to another.

Depending upon embodiment details, particular PINS systems and methods may correspond to transcranial, cortical, subcortical, deep brain, cerebellar, spinal column, cranial or other peripheral nerve, and/or other types of neural stimulation. Representative types of neural stimulation that may be employed in particular embodiments include one or more of cortical stimulation (CS), vagal nerve stimulation (VNS), deep brain stimulation (DBS), transcranial magnetic stimulation (TMS), and transcranial direct current stimulation (tDCS).

Particular types of neural stimulation devices may be partially or completely implanted in a patient, and may include one or more pulse generators coupled to a set of electrodes, electrode assemblies, and/or signal transfer devices. Such devices may comprise, for example, a cortical stimulation device as described in U.S. Patent Application Publication No. 20020087201, entitled "Methods and Apparatus for Effectuating a Lasting Change in a Neural Function of a Patient," filed on Mar. 8, 2001; a DBS device as described in U.S. Pat. No. 5,716,377; and/or a VNS device as described in U.S. Pat. No. 5,299,569, each of which is incorporated herein by reference. TMS devices may comprise a pulse generator coupled to a coil that is configured to generate a particular type of magnetic field pattern. Representative types of TMS devices may be available, for example, from The Magstim Company Ltd., Wales, UK (www.magstim.com). One representative type of tDCS device is described by W. Paulus in "Transcranial Direct Current Stimulation (tDCS)", Transcranial Magnetic Stimulation and Transcranial Direct Current Stimulation (Supplements to Clinical Neurophysiology), (2003) Vol. 56, p. 249-254, which is also incorporated herein by reference.

The neural stimulation may be applied to one or more anatomical locations. An anatomical location or region at which stimulation signals are applied or delivered to, or through, or near a target neural population may be defined as a stimulation site. A stimulation site and/or a target neural population may be identified and/or located in a variety of manners, for example, through one or more procedures involving anatomical landmark identification; structural and/or functional anatomical imaging (e.g., Magnetic Resonance Imaging (MRI), Diffusion Tensor Imaging (DTI), functional MRI (fMRI), Positron Emission Tomography (PET), Magnetic Resonance Angiography (MRA), Near-infrared Spectroscopy (NIRS) or Optical Tomography (OT), or Magnetoencephalography (MEG)); electrophysiological signal measurement (e.g., electroencephalography (EEG) or electromyography (EMG)); anatomical spectroscopy (e.g., Magnetic Resonance Spectroscopy (MRS)); and/or other techniques. Representative manners of identifying a target neural population and/or a stimulation site are provided in U.S. Patent Application Publication No. US 20020087201, and U.S. patent application Ser. No. 10/986,614, entitled "Systems and Methods for Selecting Stimulation Sites and Applying Treatment, Including Treatment of Parkinson's Disease, Other Movement Disorders, and/or Drug Side Effects," filed on Nov. 12, 2004, each of which is incorporated herein by reference in its entirety.

In various embodiments, the neural stimulation device(s) may apply or deliver stimulation signals to a patient. The stimulation signals may include electromagnetic, acoustic, thermal, and/or other types of signals (e.g., mechanical forces) capable of affecting neural function. Electromagnetic stimulation signals may be defined in accordance with spatial, temporal, electrical, and/or magnetic signal parameters, properties and/or characteristics. Such stimulation signals may take on various forms, and may be characterized by various waveform characteristics (e.g., signal amplitude, duration, duty cycle, polarity, pulse width, phase information, pulse repetition frequency, and burst frequency). Spatial, temporal, and/or waveform parameters may be varied in one or more manners to enhance a likelihood of providing, maintaining, or prolonging symptomatic relief from neurologic dysfunction. Representative types of stimulation signals and manners of generating and/or varying such signals are described in U.S. patent application Ser. No. 11/182,713, entitled "Systems and Methods for Enhancing or Affecting Neural Stimulation Efficiency and/or Efficacy," filed on Jul. 15, 2005, which is incorporated herein by reference in its entirety.

In several embodiments, a PINS-ACT system may comprise a set of neural stimulation devices configured to provide stimulation signals to a set of stimulation sites, as well as a chemical substance infusion or delivery device (e.g., an implantable drug infusion pump) configured to release or apply one or more chemical substances (e.g., an amphetamine, a pharmacologic agent, a neuroprotective agent, neurotrophic agent, a growth factor, a muscle relaxant, or another substance) to a set of delivery sites upon or within a patient's body.

A delivery site may correspond, for example, to a target neural population or a target vascular structure. A delivery site may be identified in a variety of manners, for example, through a set of procedures involving anatomical landmark identification and/or medical imaging (e.g., Magnetic Resonance Angiography (MRA)). A representative combined neural stimulation and drug infusion system that may be applicable to particular PINT embodiments is described in U.S. Pat. No. 6,782,292, incorporated herein by reference in its entirety.

In a related manner, a PICT system, subsystem, or device may comprise an infusion pump and/or other substance transfer or application device configured to apply or deliver particular chemical substances to a set of delivery sites. Representative types of implantable drug pumps that may be applicable to particular PINS embodiments are described in U.S. Pat. No. 6,764,472 and U.S. Patent Application Publication No. 20050107753, each of which is incorporated herein by reference in its entirety.

Various embodiments of PINT systems and methods may apply or deliver particular types of neural stimulation and/or chemical substances to a patient in association with adjunctive rehabilitative training (ART). Depending upon embodiment details, one or more types of neural stimulation and/or chemical substances may be provided to the patient before, during, and/or after one or more ART sessions. Any given ART session may involve one or more types of ART systems, subsystems, devices, and/or elements, which may be automated or semi-automated. Particular levels of automation may allow the patient to participate or attempt to participate in therapeutic activities without the need for continuous or nearly continuous clinician, physician or therapist presence during a session.

As described further below in association with various embodiments, ART systems, devices, or elements may be directed toward facilitating and/or effectuating patient performance of behavioral therapies, activities and/or tasks such as physical therapy; physical and/or cognitive skills training or practice, such as training in Activities of Daily Living (ADL), intentional use of an affected body part, speech therapy, vision, visual, and/or spatial perception training, a reading task, a writing task, an auditory activity (for example, a musical or rhythmic task or training), attention tasks, a cognitive activity, memory task, or memory training, comprehension tasks, and/or other therapies or activities. Representative types of ART devices or elements may include assistive clothing devices, ADL devices, visual presentation or virtual reality hardware and/or software, electronic gaming devices, touch screen devices, writing tablets, and/or other devices, which may facilitate at least some degree of physical manipulation and/or interactive participation from the patient for enhanced performance of certain types of activities involving particular neural pathways or systems, neurofunctional abilities (e.g., cognitive abilities), and/or muscle groups.

In certain embodiments, augmentative stimulation devices (ASDs) may provide augmentative stimulation in association or conjunction with rehabilitative, restorative, and/or therapeutic effects provided by particular neural stimulation and/or ART devices. An ASD may provide, for example, electrical, magnetic, optical, electromechanical, mechanical, or thermal stimulation to an individual at one or more times. An ASD may be strategically positioned relative to one or more physiologically relevant locations to augment compensatory, restorative, and/or rehabilitative effects. The augmentative stimulation may be provided by devices that are implanted, external, and/or percutaneous, and may include, by way of example, functional electrical stimulation (FES), neuromuscular electrical stimulation (NMES), TMS, and/or tDCS devices. An ASD may be operatively coupled to one or more neural stimulation, drug delivery, and/or ART devices in a manner that facilitates signal communication therewith.

In accordance with several embodiments of the disclosed invention, a PINT system and/or method may facilitate patient participation in a limited duration treatment program. A limited duration treatment program may effectuate or facilitate at least some degree of permanent, essentially permanent, or long term rehabilitation or restoration of a patient's ability to perform one or more types of physical and/or cognitive functions that had been lost or degraded due to neurologic dysfunction. Such treatment need not be directed toward managing a chronic condition that exists over a very long period of time or throughout a patient's life. Rather, the treatment may be applied over a limited time that corresponds to the extent of the patient's recovery or functional gain(s). A limited duration treatment program may comprise a set of treatment sessions involving one or more types of neural stimulation and/or chemical substances in association with one or more adjunctive therapies. Representative types of limited duration programs are described in U.S. Patent Application Publication No. US 2002/0087201, entitled "Methods and Apparatus for Effectuating a Lasting Change in a Neural-Function of a Patient," filed on Mar. 8, 2001, which is incorporated herein by reference in its entirety.

Representative PINS System Embodiments

FIG. 1A is a schematic illustration of a PINS system 1000 according to an embodiment of the invention, which may facilitate patient participation in a multi-modal neurofunctional development, treatment, or therapy program or regimen that involves neural stimulation and one or more behavioral activities. In various embodiments, a PINS system 1000 may comprise a neural stimulation system (NSS) 100, an adjunctive rehabilitative training (ART) device 300, and a therapy management computer (TMC) 800 that is configured for signal communication with the ART device 300 and possibly the NSS 100 at one or more times.

The NSS 100 may comprise one or more types of neural stimulation devices, for example, an implantable pulse generator (IPG) 110 that is coupled to a set of signal transfer devices, electrode assemblies, and/or electrodes 120. The NSS 100 may also comprise one or more types of signal or substance monitoring devices, for example, an electrode assembly configured to monitor electrocorticographic (ECoG) signals. Depending upon embodiment details, the NSS 100 may comprise fully implanted components that are surgically placed within a patient 10, as illustrated, and/or components that are partially implanted or external to the patient 10.

The NSS 100 may further comprise an external programming or communication device 130, which in some embodiments facilitates unidirectional or bi-directional communication (e.g., through magnetic or RF telemetry) between the TMC 800 and the IPG 110. Such communication may involve the transfer of configuration information, program instructions, stimulation signal parameters, power signals, and/or data. The communication device 130 may be coupled to the TMC 800 by a wire-based or a wireless link 135.

In some PINT embodiments, a communication device 130 may be coupled to a programming device (e.g., a handheld or laptop computer, not shown) other than the TMC 800, in a manner understood by those skilled in the relevant art. In certain embodiments, a programming device such as a handheld computer may be configured for communication with the TMC 800. Such communication may correspond in particular embodiments to the selection and/or modification of neural stimulation and/or monitoring parameters.

In addition to or as an alternative to the foregoing, in some embodiments a PINT system (such as the PINS system 1000 shown in FIG. 1A or essentially any other type of system in accordance with the present invention) may comprise a patient based IPG activation device, communication puck, or patient magnet 131 to which the IPG 110 is responsive, in a manner understood by those skilled in the art. The patient based activation device 131 may be carried, worn, or held by the patient 10. In response to patient based activation, the IPG 110 may power on or off, and/or perform particular types of neural stimulation and/or monitoring operations. The neural stimulation operations may involve the application or delivery of neural stimulation signals in accordance with one or more sets of preprogrammed stimulation parameters. A patient-based activation device and/or preprogrammed or preselected sets of stimulation parameters, may facilitate remote or home based therapies.

In general, the ART device 300 may comprise a set of electrical, magnetic, and/or mechanical elements, devices, and/or components that facilitate or effectuate patient performance of activities that are relevant to the restoration or development of particular types of neurofunctional abilities. Depending upon embodiment details, an ART device 300 may comprise a set of devices, mechanisms, and/or structures that 1) the patient 10 moves or manipulates; 2) moves or manipulates one or more patient body parts; and/or 3) provides sensory and/or proprioceptive stimulation (e.g., through the application or conveyance of electrical, vibratory, thermal, auditory, visual, and/or olfactory signals) to the patient 10 at one or more times.

In several embodiments, the TMC 800 comprises a computer, computer system, and/or computer-readable medium that provides 1) an adjunctive training user interface corresponding to the ART device 300, where the user interface may present audio, visual, and/or other adjunctive training information to the patient 10; and (in at least some embodiments) 2) a programming, control, and data transfer interface corresponding to the NSS 100. As further detailed below, the TMC 800 may determine, analyze, evaluate, estimate, and/or categorize patient performance based upon signals received from the ART device 300. In some embodiments the TMC 800 may affect or control the application of neural stimulation signals to the patient 10, possibly based upon the nature of intended patient tasks and/or patient performance during one or more ART sessions. The TMC 800 may additionally serve as a network node that facilitates the transfer of patient-related information to other local or remote systems or devices.

One or more of the NSS 100, the ART device 300, and the TMC 800 may vary in structure and/or function in accordance with a wide range of embodiment details. For example, portions of one or more ART device elements may be implemented by particular elements of the TMC 800. Specific aspects of particular embodiments of each of the NSS 100, the ART device 300, and the TMC 800 are described in detail hereafter.

Before, during, and/or after an ART session, the NSS 100 applies or delivers one or more types of stimulation signals to one or more target neural populations, as further detailed below. In certain instances, it may be desirable to associate, combine, or incorporate cortical stimulation with the rehabilitation or development of one or more body parts, for example, an upper extremity that has been affected by a stroke. Thus, in one embodiment, the NSS 100 comprises a cortical and/or other type of neural stimulation system having at least one IPG 110; one or more electrode assemblies or electrodes 120 implanted at or relative to a set of target neural populations, for example, particular epidural and/or subdural cortical stimulation sites (e.g., one or more portions of the patients motor cortex, premotor cortex, somatosensory cortex, prefrontal cortex, and/or another region in one or both hemispheres of the cerebral cortex 12); and possibly a set of links or lead wires 115 that couple the IPG 110 to the electrode assemblies 120. In certain embodiments, the NSS 100 may comprise one or more microstimulators (e.g., a Bionic Neuron or BION®, manufactured by Advanced Bionics of Sylmar, Calif.) and possibly other microdevices, in which case the lead wires 115 may be omitted.

The IPG 110 can comprise components such as instruction processing, pulse generating, and communication circuitry that reside within a biocompatible housing. The IPG 110 can further comprise a power source (e.g., a battery and/or a capacitor) and associated power circuitry. In some embodiments, the IPG 110 can also comprise one or more electrical contacts or circuit completion elements that reside or are formed upon the IPG's housing, which may facilitate a unipolar stimulation configuration. The IPG 110 also comprises a computer readable, operable, and/or programmable medium (e.g., a memory and/or a register set) capable of storing configuration information, program instructions, stimulation parameter information, and/or data. The pulse generating circuitry outputs stimulation signals, which are delivered to one or more electrode assemblies 120 at one or more times.

An electrode assembly 120 may comprise a set of electrical contacts 122 that may be carried by a substrate, and which are configured for placement or implantation at a stimulation site. An electrode assembly 120 may be of any number of dimensions, shapes and sizes and may be placed at one or more locations as desired or indicated based upon the nature of an individual's neurologic condition. Moreover, in certain embodiments, a subset of contacts 122 may be selectively activated at particular times and/or in various patterns to facilitate enhanced stimulation efficacy. Additional representative electrode assembly embodiments are described in U.S. patent application Ser. No. 10/742,579, entitled "Apparatuses and Systems for Applying Electrical Stimulation to a Patient," filed on Dec. 18, 2003, incorporated herein by reference in its entirety.

As indicated above, the NSS 100 may also comprise a programming or communication device 130 that facilitates or effectuates unidirectional or bi-directional signal communication with the TMC 800. The communication device 130 may comprise, for example, a housing in which a coil and wireless communication circuitry reside. In some embodiments, the TMC 800 may initiate, continue, adjust, query, interrupt, restart, and/or discontinue neural stimulation by issuing or outputting one or more commands, instructions, and/or parameters that are transferred to the IPG 110 by way of the communication device 130. The TMC 800 may issue such commands based upon signals received from an ART device 300 during one or more ART sessions.

The ART device 300 may comprise various types of components that facilitate and/or effectuate the movement, manipulation, and/or sensory stimulation of an affected limb such as a hand 22 and/or an arm 20 as shown in the instant Figure. In one embodiment directed toward the restoration or development of hand/wrist function, the ART device 300 comprises a base 310, an armrest 312, and a joystick or joystick-type mechanism 320. The ART device 300 is coupled to the TMC 800 by a link 325, which may be wire-based or wireless.

During an ART session, the joystick 320 may be grasped by the patient's hand 22 and moved, manipulated, directed, carried, and/or rotated through one or more types of movements or movement patterns. In some embodiments, during one or more portions of a movement or movement pattern, the joystick 320 may apply assistive, resistive/opposing, stabilizing, and/or destabilizing forces to the patient's hand 22 to affect the patient's hand movements or movement patterns. The joystick 320 may include one or more buttons and/or levers that are responsive to finger or thumb pressure. Such buttons or levers may have programmably assigned functionality, in a manner understood by those skilled in the relevant art.

As described in greater detail below, the TMC 800 may present auditory and/or visual (A/V) adjunctive training information (e.g., instructions or motivational patient performance feedback) to the patient 10; and/or the joystick 320 may apply or convey particular sensory stimuli to the patient 10. The auditory, visual, and/or other sensory stimuli may correspond to a video game, a virtual reality presentation, educational information, a cognitive task or test, and/or essentially any type of activity or task that is relevant to improving the patient's neurofunctional condition. The patient 10 is expected or encouraged to interactively respond to such stimuli using the joystick 320.

Depending upon embodiment details or the nature of an individual's neurologic condition and/or neurofunctional development progress, the IPG 110 may output stimulation signals during one or more portions of an ART session in a manner that is independent of or dependent upon signals that the TMC 800 receives from the ART device 300, as further described below.

Figure 1B:
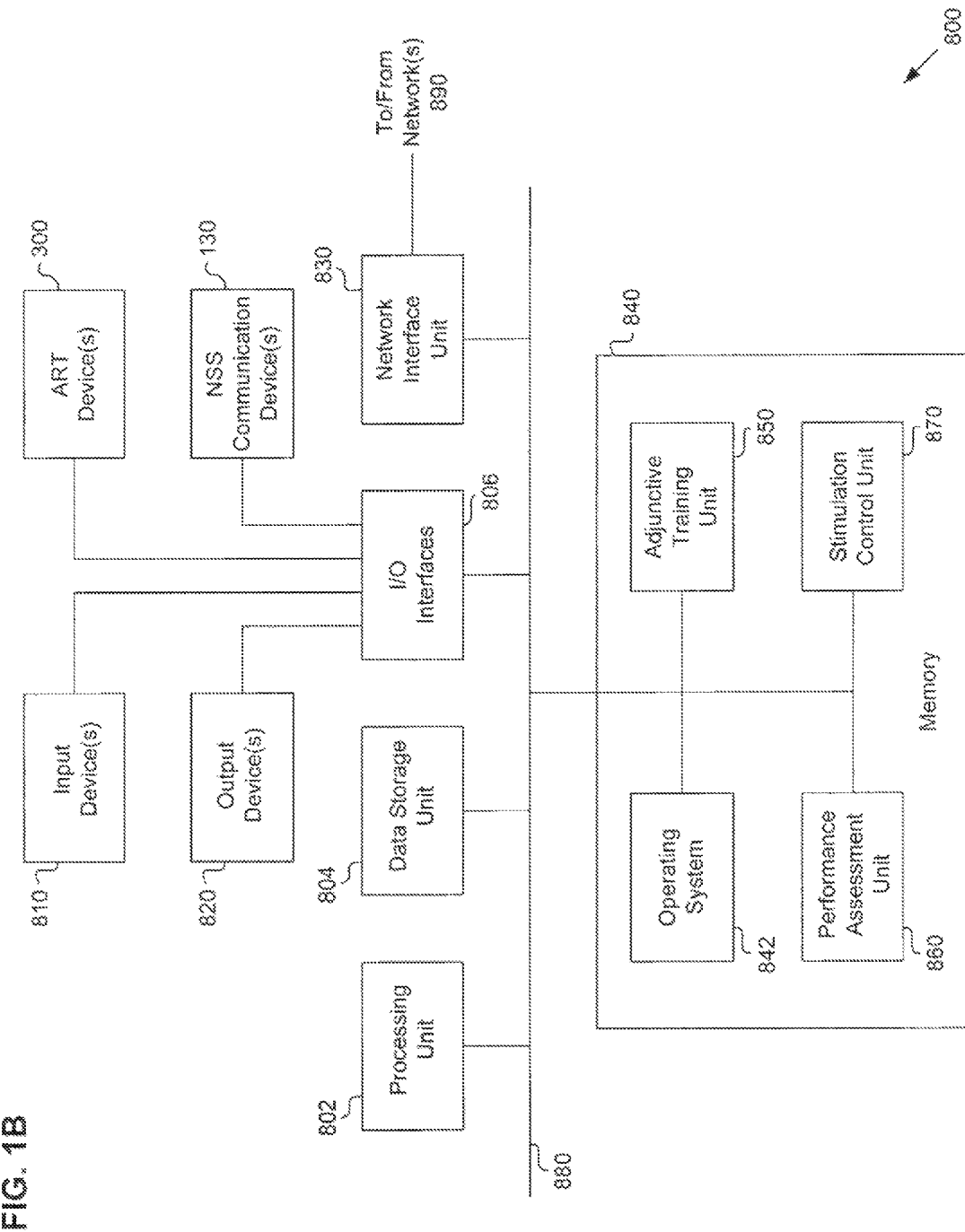
FIG. 1B is a block diagram of a therapy management computer (TMC) according to an embodiment of the invention.

FIG. 1B is a block diagram of a TMC 800 according to an embodiment of the invention. Relative to FIG. 1A, like reference numbers correspond to like elements. In one embodiment, the TMC 800 comprises a computer system having at least one processing unit 802; a data storage unit 804; a set of input/output (I/O) interfaces 806; a set of input devices 810; a set of output devices 820; a network interface unit 830; and a memory 840 wherein an operating system 842, an adjunctive training unit (ATU) 850, a performance assessment unit (PAU) 860, and a stimulation control unit (SCU) 870 reside. Particular elements of the TMC 800 may be coupled to a set of common buses 880 in a manner understood by those skilled in the art.

The TMC 800 may also be coupled a network 890, which may comprise one or more of a Local Area Network (LAN), a Wide Area Network (WAN), the Internet, a telephone network (e.g., the Public Switched Telephone Network (PTSN) and/or a cellular network), a satellite network, and/or another type of communication infrastructure that facilitates interactive, real-time, isochronous, and/or delayed information transfer. In some embodiments, the network 890 may facilitate information transfer to and/or from one or more network attached storage (NAS) devices, servers or server farms, and/or databases (e.g., a medical database).

The processing unit 802 may comprise a microprocessor capable of executing program instructions. The data storage unit 804 may comprise one or more fixed and/or removable data storage media, for example, a hard disk drive capable of storing program instructions and/or data. The set of I/O interfaces 806 may comprise one or more standard and/or proprietary I/O interfaces, for example, a Universal Serial Bus (USB) interface, an IEEE-1394 or Firewire™ interface, a serial port, and/or a parallel port.

The set of I/O interfaces 806 may be coupled to a set of input devices 810, a set of output devices 820, one or more ART devices 300, and possibly one or more NSS communication devices 130. In certain embodiments, a single TMC 800 may manage or direct multiple local or remote ART sessions, possibly in a simultaneous or nearly simultaneous manner. The set of I/O interfaces 806 may include hardware (e.g., a video card) and/or software (e.g., drivers) that facilitate communication with particular types of devices. The set of input devices 810 may comprise one or more of a keyboard 812 and a mouse 814, a camera or image capture device 816, a microphone 818, and/or another type of device. The set of output devices 820 may comprise one or more of a display device (e.g., a computer monitor) 822, a set of speakers 824, and/or another type of device.

The memory 840 may comprise a computer readable, operable, and/or programmable medium having one or more types of volatile and/or nonvolatile data storage elements, for example, a Random Access Memory (RAM) and a Read Only Memory (ROM). The operating system 842 may comprise a set of programming instructions that manage access to TMC system-level hardware and/or software resources, in a manner understood by those skilled in the art.

The ATU 850 may comprise a set of program instructions that generates or manages the presentation of adjunctive training information to the patient 10. The ATU 850 may comprise program instructions corresponding to or directed toward implementing and/or managing a video game; a virtual reality environment or activity scenario; various types of physical and/or cognitive tasks; standardized or customized neurofunctional capability or assessment tests; and/or other activities, situations, tasks, or tests.

The PAU 860 may comprise a set of program instructions that receives, analyzes evaluates, categorizes, and/or stores patient performance information associated with one or more ART sessions. Depending upon embodiment details, the patient performance information may comprise signals received from one or more ART devices 300, still and/or video images captured by a camera 816, scores associated with performance evaluation tests, and/or other information. The PAU 860 may analyze such information on a regular or periodic basis, and/or in response to a request received from a medical professional or the patient 10. In certain embodiments, particular patient performance information may be defined, analyzed, and/or stored at a remote location (e.g., by program instructions executing upon a remote computer coupled to the network 890).

The SCU 870 may comprise a set of program instructions that manage the application or delivery of neural stimulation signals to the patient 10. As elaborated upon below, the SCU 870 may manage the issuance of signals to and/or the receipt of signals from the NSS 100, possibly based upon patient performance as determined or estimated by the PAU 860.

The ATU 850, the PAU 860, and/or the SCU 870 may operate in a wide variety of manners to facilitate a patient's neurofunctional development through neural stimulation in association with automated and/or semi-automated interactive patient activities. Particular manners in which the ATU 850, the PAU 860, and/or the SCU 870 may direct or manage patient interactive neural stimulation are described in detail below.

Figure 2:
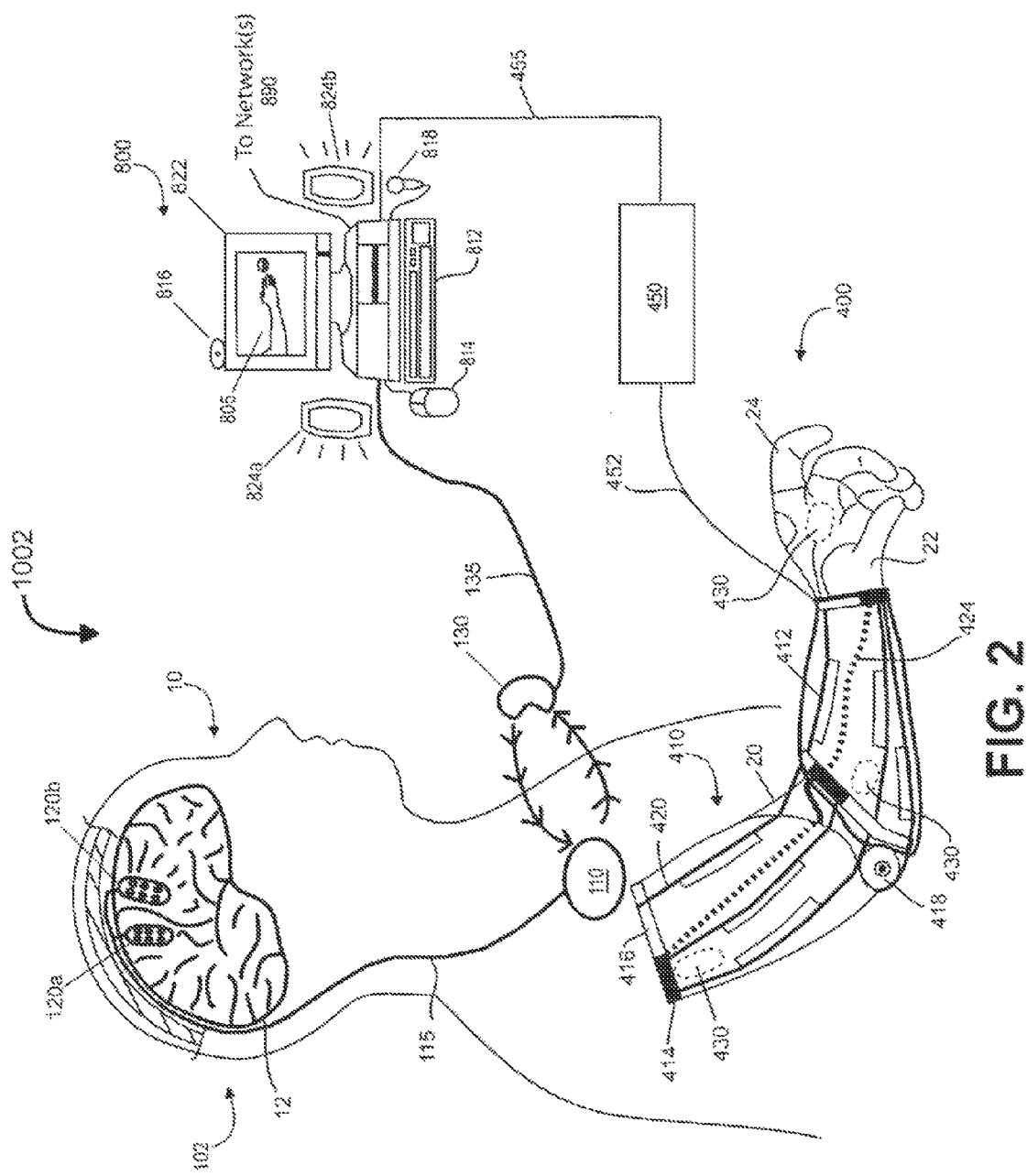
FIG. 2 is a schematic illustration of a PINS system according to another embodiment of the invention.

FIG. 2 is a schematic illustration of a PINS system 1002 according to another embodiment of the invention. In various embodiments, a PINS system 1002 may comprise a neural stimulation system (NSS) 102, an assistive clothing ART (AC-ART) device 400, and a TMC 800 configured for signal communication with the AC-ART device 400 and/or the NSS 102 at one or more times.

In several embodiments, the structure and/or function of the NSS 102 and TMC 800 may be identical, essentially identical, or similar to that described above with reference to FIGS. 1A and 1B, and hence like or analogous reference numbers may indicate like or analogous elements. In the instant Figure, the NSS 102 may comprise a set of electrode assemblies 120a, 120b, at least one of which includes a set of electrical contacts 122. A given electrode assembly 120a, 120b may be implanted at or relative to one or more anatomical locations, and may apply stimulation signals, and/or detect, sense, monitor, or measure particular types of physiologic or physiologic correlate signals, chemical substance levels, temperature, and/or other information. Depending upon embodiment details, a set of lead wires 115 may couple the electrode assemblies 120a, 120b to one or more pulse generators 110.

In some embodiments, signals may be communicated to and/or received from two or more neuroanatomical locations, which may correspond to the same or different brain hemispheres. Electrode assemblies 120a, 120b may be implanted at neurological locations that may be functionally related (e.g., associated by way of a temporally-sequenced neural signaling pathway; or in homologous locations), generally distinct, or distinct. In a general example, an electrode assembly 120a may be positioned at or relative to an epidural and/or subdural cortical location that is functionally responsible for movement of an affected limb. Another electrode assembly 120b may be placed at a neurological location that is functionally responsible for providing neurological sensory information corresponding to the affected limb, such as an arm 20 and/or another body part.

As another representative example, one or more electrode assemblies 120a positioned at or relative to particular neuroanatomical locations (e.g., a set of cortical, subcortical, and/or spinal cord locations) may apply stimulation signals, and one or more other electrode assemblies 120b positioned at or relative to certain anatomical locations may sense or measure particular types of signals, for example, ECoG, cerebral blood flow (CBF), blood composition or, oxygenation state, EMG, and/or other types of signals. Sensing or monitoring activity may occur in the vicinity of the neural stimulation, and/or at other locations.

In various embodiments, the AC-ART device 400 may comprise an apparel-type device that is positioned relative to and/or worn upon an affected limb or extremity, such that it facilitates patient performance of behavioral therapy and/or rehabilitation activities during one or more therapy periods, treatment sessions, or training sessions. The patient 10 may participate in such activities in a clinical setting, or in another setting such as a home environment. Patients 10 experiencing neurologic dysfunction associated with hemiparesis, spasticity, neglect, bradykinesia, and/or other conditions may benefit from an AC-ART device 400 configured to provide physical, sensory, and/or proprioceptive manipulation or stimulation of body parts such as an arm 20, a hand 22, and fingers 24, and possibly lower extremity body parts such a leg and/or a foot. A representative type of assistive clothing device that may be suitable for use in particular embodiments of the invention is described in detail in US Patent Application Publication No. 2003/0120183, entitled "Assistive Clothing," incorporated herein by reference in its entirety.

In certain embodiments, the AC-ART device 400 may comprise a wearable sleeve apparatus 410 coupled to a controller 450 by a wire-based or wireless link 452. Depending upon embodiment details, one or more portions of the controller 450 may be separate from, carried by, or integral with the sleeve apparatus 410. The controller 450 may further be coupled to the TMC 800 by another wire-based or wireless link 454. Additionally or alternatively, in certain embodiments one or more portions of the controller 450 may be implemented by particular elements of the TMC 800.

As shown, an AC-ART device 400 may be worn about portions of a patient's limb(s) 20, for example, the arm 20, wrist, and/or hand 22, to selectively facilitate and/or inhibit particular types of movement or motion. For example, the patient 10 may wear the AC-ART device 400 by placing the sleeve apparatus 410 about an arm 20 and hand 22. The sleeve apparatus 410 may comprise support materials that surround, hold, or carry portions a limb 20; as well as one or more motion or activity facilitation devices, mechanisms, or structures. Depending upon embodiment details, motion facilitation or motion control devices may include translational actuators 412, rotational actuators 414, rotation cuffs 416, pivots 418, cables or cords 420, electrical couplings 424, and/or other elements that facilitate, direct, or manage the rotation, flexion, or extension of the patient's arm, wrist, and/or hand 22, possibly based upon an extent to which a patient 10 can independently or successfully perform one or more movements as further described below. Several types of motion control devices (e.g., actuators 412, 414) may be responsive to signals or commands received from the controller 450.

The AC-ART device 400 may additionally comprise a set of sensors 430 that facilitate sensing, detection, measurement, monitoring, characterization, outputting, and/or control of positions, orientations, velocities, forces, and/or other information corresponding to particular portions of the sleeve apparatus 410 in one or more directions or dimensions. In several embodiments, particular types of sensors 430 (e.g., ultrasonic transducers; force, torque, or pressure sensors; accelerometers; EMG electrodes, and/or other devices) may be carried by the sleeve apparatus 410. Additionally or alternatively, in some embodiments, one or more portions of certain sensors 430, sensing elements, or sensing systems may be separate from the sleeve apparatus 410 (e.g., a set of room-based radio frequency (RF) position/orientation sensors). In certain embodiments, actuators 412, 414, rotation cuffs 416, and/or other elements may be capable of receiving and/or outputting such information.

The actuators 412, 414, rotation cuffs 416, and cables 420 may be located upon or about the sleeve apparatus 410 in a manner that facilitates or controls an intended range or type of body part motion, thereby facilitating patient performance of activities that may be relevant to rehabilitating, restoring, or augmenting certain neurofunctional abilities. In various embodiments, the translational actuators 412 may be configured with cables 420 to facilitate translational motion and the rotation cuffs 416 may be configured with rotational actuators 414 to facilitate rotational motion between particular portions of the sleeve apparatus 410. Electrical couplings 424 may facilitate signal transfer between particular actuators 412, 414 and the controller 450, and/or between actuators 412, 414 themselves.

In a representative embodiment, one or more actuators 412, 414 may comprise a set of stepper motors configured to provide or apply forces in lateral, longitudinal and/or oblique or diagonal directions. Although electromechanical actuators are described in relation to this embodiment, it is to be appreciated that other types of actuators suitable for use in various embodiments may comprise pistons, magnetic mechanisms, and/or other devices without departing from the scope of the invention.

In some embodiments, one or more pivots 418 may be carried by or located upon the device 410 to generally coincide with a bending point on the patient's limb, and may likewise be coupled to certain cables 420 to facilitate such motion. For instance, in this illustrated example, a pivot 418 may facilitate bending motion at an elbow. However, inasmuch as an AC-ART device 400 may be worn about other body parts (e.g., the legs or torso), a pivot 418 may be configured to correspond to other bending locations (e.g., knees, ankles, or the hip area).

The controller 450, e.g., in association with the TMC 800, may initiate, measure, increase, decrease, interrupt, continue, or terminate the application of forces to the sleeve apparatus 410 to enable, oppose, and/or characterize particular patient motions. The controller 450 may comprise hardware and/or software sending information to and/or receiving information from the sleeve apparatus 410. Such information may comprise, for example, commands directed to particular actuators 412, 414 or rotation cuffs 416, or position/orientation signals received from one or more sensors 430. The controller 450 may also comprise hardware and/or software for sending information to and/or receiving information from the TMC 800. For example, the controller 450 may transfer real time, near-real time, and/or stored or time stamped actuator force data, sleeve apparatus position/orientation measurements, and/or other information to the TMC 800. As another example, the TMC 800, possibly based upon current and/or past sleeve apparatus position(s) or patient performance, may transfer fully and/or partially assistive or resistive motion commands; fully and/or partially assistive or resistive motion scripts, programs, or corresponding identifiers (IDs); performance monitoring requests; and/or other information to the controller 450.

In various embodiments, the controller 450 may comprise one or more processing units; one or more types of electronically readable, writable, and/or programmable media (e.g., a fixed and/or a removable memory, a set of buffers, and the like), which may store program instructions and/or data; signal conversion circuitry (e.g., analog to digital (ND) converters); signal communication circuitry (e.g., I/O circuitry, software drivers, wireless or wire-based communication ports, and the like); and/or other elements.

The TMC 800 may comprise a computer system configured to communicate with the controller 450 and/or the NSS 100 at one or more times. Depending upon embodiment details, the TMC 800 may be configured and adapted to facilitate one or more of the following:

1) Communication with the NSS 100, which may involve the transfer of neural stimulation parameters, commands directed toward a pulse generator or implanted monitoring device, physiologic or physiologic correlate information corresponding to such monitoring devices, patient data, and/or other information. Through such communication, the TMC 800 may initiate, continue, query, adjust, monitor, interrupt, and/or terminate neural stimulation and/or implanted device monitoring operations before, during, and/or after particular portions of a therapy period or treatment session.

2) Communication with the controller 450, which may involve the transfer of commands, requests, scripts or script IDs, sleeve apparatus parameters (e.g., applied or measured force signals or data, position/orientation data, and the like), and/or other information.

3) Presentation of information to the patient 10. Such information may comprise auditory and/or visual patient instructions, ideal or example movement patterns, images, or image sequences, interactive virtual reality situations involving particular behavioral activities, patient motions, and situational goals or targets, real time or near-real time patient movement images 805, visual and/or auditory patient performance feedback, which may include motivational or behavior reinforcement feedback, and/or other information.

4) Acquisition (e.g., using an image or video capture device 816), storage, retrieval, measurement, characterization, and/or analysis of patient related information (e.g., sleeve apparatus signals corresponding to an extent to which the patient 10 performs particular reaching, pointing, grasping, pushing, pulling, lifting, releasing, or other tasks).

5) Selection or modification of virtual reality situations, behavioral activities, and/or sleeve apparatus scripts, script IDs, or parameters (e.g., applied forces), possibly based upon actual or estimated current and/or past patient performance.

6) Remote communication of patient-related information, which may involve the transfer of information to a networked computer system or device (e.g., used by a clinician or physician), and/or the receipt of commands, instructions, messages (e.g., an A/V message) and/or other information from a networked computer system.

In general, a treatment program or regimen may specify or indicate one or more sets of therapy period or treatment session parameters. Such parameters may correspond to therapy period or treatment session duration, particular behavioral activities, sensory stimuli, neural stimulation parameters, implanted device monitoring instructions, and/or AC-ART device parameters across one or more time domains (e.g., a subseconds-based, a seconds-based, an hours-based, a week-based, a month-based, or other time domain). One or more portions of a treatment program may be based on human and/or PINS-based assessments of the patient's neurofunctional capabilities.

In various situations, new or updated therapy period or treatment session parameters may be needed or desirable. Such situations may arise, for example, when a patient 10 is a first-time user; initial or periodic measurement or estimation of a patient movement threshold (e.g., using of EMG electrodes or sensors 430 to detect patient motion) is desirable (e.g., once per session or once per week) to facilitate determination of certain neural stimulation parameters (e.g., peak current level, pulse repetition frequency, and/or pulse width); particular patient functional gains have begun to plateau or peak; and/or the patient 10 is resuming a treatment program following an interruption period (e.g., after a rest, strengthening, or neural consolidation period). In various embodiments, TMC 800 and/or the controller 450 may initiate a diagnostic session to determine various parameters.

In some embodiments, the TMC 800 may direct the NSS 100 to apply neural stimulation signals and/or activate implanted monitoring devices during one or more portions of a diagnostic session. Additionally, the TMC 800 and/or the controller 450 may acquire, sense, monitor, or measure patient motion, activity, and/or responses. In certain embodiments, during a diagnostic session the TMC 800 and/or the controller 450 may specify or select particular types of test exercises or movements for the patient 10 to perform using the sleeve apparatus 410.

The TMC 800 may acquire, retrieve, store, characterize, and/or analyze diagnostic session information, and possibly transfer diagnostic session information to a remote location for clinician or physician analysis. Based upon diagnostic session information analysis, a medical professional and/or the TMC 800 may select, define, or adjust therapy period or treatment session parameters.

The nature of a therapy period or treatment session may vary based upon the patient's neurofunctional condition; current and/or past patient capabilities, performance, and/or progress; and/or embodiment details. In some embodiments, during a treatment session the AC-ART device 400 may completely or partially guide or carry the patient 10 through one or more movement patterns before, during, and/or after the NSS 100 applies neural stimulation to the patient 10. Additionally or alternatively, the AC-ART device 400, possibly in association with the TMC 800, may adjust or adapt various types (e.g., assistive or oppositional longitudinal or rotational) of forces applied by the sleeve apparatus 410 at one or more times to facilitate patient performance of assisted, partially assisted, unassisted, partially opposed, and/or opposed patient movements. Manners in which such forces are applied may be based upon current or past patient performance or capabilities. In certain embodiments, the TMC 800 may initiate, continue, query, adjust, interrupt, or discontinue the application of neural stimulation signals to the patient 10 before, during, and/or the patient performs or attempts particular movements, possibly based upon present or prior patient-related information. The TMC 800 may further manage or direct the application of neural stimulation to the patient 10 in an anticipatory or approximately anticipatory manner based upon expected and/or prior patient movements.

In particular embodiments, the TMC 800 and/or the controller 450 may acquire, receive, characterize, and/or analyze signals from one or more sensors 430 to determine or estimate patient capabilities (e.g., assisted, partially assisted, or unassisted range of motion limits or movement duration) and/or patient exertion level at one or more times. The TMC 800 may additionally receive, characterize, and/or analyze signals from a set of implanted monitoring devices to determine or estimate changes in patient state information, such as changes in brainwave patterns (e.g., which may be associated with a level of patient concentration, exertion, or fatigue) corresponding to particular activities, performance results, times, and/or time intervals.

Figure 3:
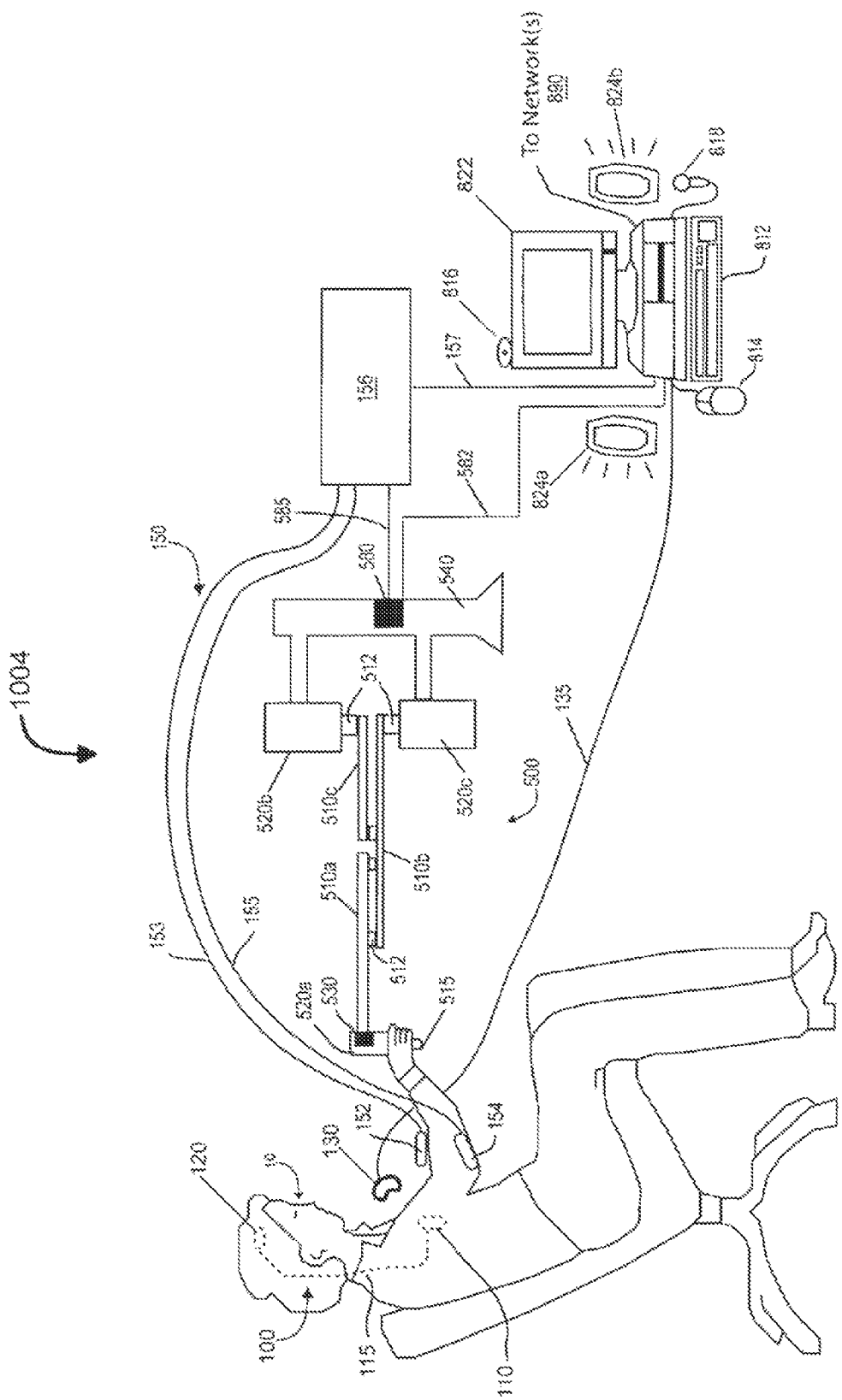
FIG. 3 is a schematic illustration of a PINS system according to another embodiment of the invention.

FIG. 3 is a schematic illustration of a PINS system 1004 according to another embodiment of the invention. In various embodiments, a PINS system 1004 may comprise a neural stimulation system (NSS) 100; a robotic ART (Rob-ART) system, apparatus, or device 500; a TMC 800; and possibly a secondary stimulation and/or monitoring (SSM) system or device 150. The TMC 800 may be configured for signal communication with the Rob-ART device 500, the NSS 100, and/or the SSM system 150 at one or more times.

In a manner identical or analogous to that described above with reference to FIGS. 1A and 2, the NSS 100 may comprise a set of neural stimulation devices, for example, one or more electrode assemblies 120 coupled to an IPG 110. The NSS 100 may be adapted for bi-directional communication with a communication device 130. In several embodiments, the communication device 130 is coupled to the TMC 800, thereby facilitating the transfer of configuration information, program instructions, stimulation signal parameters, power signals, and/or data between the TMC 800 and the NSS 100. As further described below, in such embodiments the TMC 800 may initiate, query, modify, interrupt, resume, continue, or terminate operation of the NSS 100, possibly based upon information (e.g., signals corresponding to patient performance) received from the Rob-ART device 500. In some embodiments, the communication device 130 may additionally or alternatively be configured for wire-based or wireless communication with a programmer (e.g., a handheld computer, not shown), which itself may be configured for wire-based or wireless communication with the TMC 800.

In general, a Rob-ART device 500 may comprise one or more types of robotic systems, devices, and/or elements configured and adapted to enable, assist, resist, and/or oppose particular type of body part (e.g., hand, arm, leg, or foot) motions or movement patterns. A Rob-ART device 500 may further comprise particular types of sensing or monitoring devices or elements (e.g., force, velocity, and position sensors) that facilitate the generation, retrieval, measurement, analysis, and/or characterization of Rob-ART motion-related signals corresponding to patient movements or patient performance. A Rob-ART device 500 additionally comprises a controller for directing or managing the operation of its robotic and sensing elements. The controller may comprise hardware (e.g., signal conversion circuitry; a computer readable or programmable medium; an instruction and/or signal processing unit or microcontroller; and power/power management circuitry) and software, in a manner understood by those skilled in the art. The Rob-ART controller may be separate or generally separate from the TMC 800; and/or may comprise particular elements (e.g., a set of circuit boards carrying integrated circuits that facilitate Rob-ART operation) of, within, or carried by the TMC 800.

In various embodiments, a Rob-ART device 500 may guide, carry, move, or manipulate particular body parts (e.g., a hand, arm, leg, or foot) in accordance with motion patterns that are expected to be therapeutic. In some embodiments, a Rob-ART device 500, possibly in association with the TMC 800, may enable, assist, resist, or oppose particular types of patient motion based upon an extent to which the patient 10 can independently or successfully perform such motions. An extent to which the patient 10 can independently or successfully perform particular motions may be indicated by signals generated or measured by one or more Rob-ART elements (e.g., actuators or sensors), where such signals may be analyzed or characterized by the Rob-ART controller and/or the TMC 800. In certain embodiments, the TMC 800 may communicate with the NSS 100 to establish or adjust particular neural stimulation parameters based upon present or historical patient performance.

In embodiments such as that shown in FIG. 3, a Rob-ART device 500 may comprise a set of arm members 510a-c; one or more elbow joints 512 coupled to arm members 510a-c to form rotational axes; a set of actuators 520a-c configured to facilitate particular types of arm member motion; a set of sensors 530 configured to sense and quantify position, force, speed, and/or other information corresponding to particular arm members 510a-c or elbow joints 512; at least one gripping portion 515 configured for grasping by a patient's hand(s) 22; a support base 540; and a control unit 580 that is coupled to the actuators 520 and the sensors 530. The control unit 580 may further be configured for wire-based or wireless communication with the TMC 800, such as by way of a link 582. The control unit 580 may execute commands, instructions, or programs; transmit actuator and/or sensor commands; monitor, receive, process, and/or analyze actuator and sensor signals; and possibly communicate with the TMC 800 to facilitate or effectuate Rob-ART device operation. In a representative embodiment, one or more portions of the Rob-ART device 500 may be based upon or implemented using a type of robotic therapy device described in U.S. Pat. No. 5,466,213 entitled, "Interactive Robotic Therapist", which is incorporated herein by reference in its entirety.

The Rob-ART device 500 may provide one or more types of activities relevant to the restoration or development of neurofunctional abilities associated with the patient's hand 22 and/or arm 20. In situations where a patient's dysfunction may prohibit them from grasping the gripping portion 515 sufficiently on their own, the Rob-ART device 500 may include an adaptation apparatus (not shown) to attach or couple the patient's hand 22 and/or arm 20 to particular portions (e.g., an arm member 510a) of the Rob-ART device 500.

The TMC 800 comprises a computer system having a structure and/or function that is identical, essentially identical, or analogous to that described above with reference to FIGS. 1A, 1B, and 2. For example, the TMC 800 may communicate with the NSS 100 to initiate, query, continue, adjust, interrupt, resume, or discontinue neural stimulation and/or monitoring operations. The TMC 800 may also communicate information to the patient 10, such as auditory or visual instructions (e.g., still or video images indicating how a movement or motion sequence should be performed). In certain embodiments, the TMC 800 may manage, respond to, initiate, adjust, interrupt, resume, continue, or terminate Rob-ART device operation. Additionally, the TMC 800 may select particular Rob-ART programs or scripts for therapeutic and/or patient testing or evaluation purposes, possibly in an adaptive or patient performance dependent manner. The TMC 800 may further capture, receive, store, analyze, characterize, and/or transfer (e.g., to a networked system or device) patient-related information, including patient performance signals, images, and/or videos. The TMC 800 may additionally provide or present auditory or visual feedback (e.g., by playing an audio or video file that includes therapist or clinician comments) to the patient 10.

As indicated above, in several embodiments a PINT system may comprise an SSM system or device 150, which may be configured for wire-based and/or wireless communication with the TMC 800 and/or an ART system or device. Such embodiments may include the PINS system 1004 illustrated in FIG. 3, as well as other PINS and/or PICT embodiments relating or corresponding to particular Figures described herein. In general, an SSM device 150 may provide stimulation signals to the patient 10; and/or detect, monitor, or measure patient state or patient response signals. Depending upon embodiment details, the stimulation signals may comprise electromagnetic, vibratory, thermal, and/or other types of signals. Patient state or response signals may comprise EEG or EMG signals; structural and/or functional imaging signals (e.g., MRI, fMRI, PET, optical imaging, or MEG signals); intrinsic or extrinsic patient motion signals (e.g., as detected by an accelerometer or gyroscope); and/or signals corresponding to temperature, pulse rate: blood pressure, blood oxygenation or composition characteristics, blood flow, and/or other patient parameters.

Depending upon embodiment details, an SSM system 150 may apply stimulation signals and/or detect patient state or response signals at or relative to various anatomical locations based upon signal type and SSM element configuration. For example, in some embodiments, the SSM system 150 may generate or output electromagnetic signals directed toward Functional Electrical Stimulation (FES), and detect or measure EMG signals corresponding to muscle innervation at a patient's arm 20 or other extremity. In such embodiments, the SSM system 150 comprises a set of stimulation electrodes 152 and a set of sensing electrodes 154 that are configured for signal communication with a control module 156, for example, by way of stimulation and sensing links 153, 155 respectively.

Depending upon embodiment details, the control module 156 may comprise hardware (for example, communication circuitry, instruction and/or signal processing circuitry, an electronically readable or programmable medium (e.g., a memory), signal conversion circuitry, pulse generating circuitry, and power/power management circuitry) and software that facilitate the receipt and analysis of EMG signals and the selective output of electromagnetic stimulation signals. The control module 156 may be coupled to the TMC 800 and/or the Rob-ART device 500 such that the TMC 800 and/or the Rob-ART device 500 may track and/or manage certain aspects of SSM system operation. The control module 156 may communicate with the Rob-ART device 500 (e.g., by way of a link 585), and/or the TMC 800 (e.g., by way of another link 157), in accordance with one or more custom or standardized signal transfer protocols (e.g., a packet or message based protocol), in a manner understood by those skilled in the art.

In some embodiments, the control module 156 may transfer sensed EMG signals to the TMC 800 and/or the Rob-ART device 500 at one or more times. Depending upon embodiment details, the TMC 800 may adjust neural stimulation parameters; or the TMC 800 and/or the Rob-ART device 500 may adjust Rob-ART device operation at one or more times in a manner that corresponds to such EMG signals. Additionally or alternatively, in response to sensed EMG signals, the TMC 800 and/or the Rob-ART device 500 may command the SSM system 150 to apply or deliver a set of FES signals to the patient 10, possibly based upon 1) an actual, estimated, and/or inferred position or orientation of a patient extremity such as an arm 20; 2) one or more corresponding actual, estimated, and/or inferred muscle or muscle group states; 3) an extent to which the patient 10 can spatially and/or temporally move, manipulate, or direct the Rob-ART device 500 in an independent or successful manner; 4) an actual, estimated, or inferred time at which the NSS 100 delivers or applies neural stimulation signals to one or more stimulation sites; and/or 5) a measured or estimated nerve signal conduction time or latency between an NSS stimulation site and an FES stimulation site. Such a nerve signal conduction time may be determined through a set of evoked potential tests prior to a therapy period or treatment session, for example, using TMS and EMG, in a manner understood by those skilled in the art.

In certain embodiments, the SSM system 150 may comprise a set of microstimulators (e.g., one or more BIONS®) implanted relative to particular muscle and/or nerve locations to apply FES and/or detect nerve action potentials. The SSM system 150 may include a wireless communication device (e.g., a coil) that is coupled to a handheld, stand-alone, or other type of control module 156 to facilitate signal transfer to and/or from particular microstimulators. In a representative embodiment, such an SSM system 150 may be implemented in a manner described or indicated in U.S. Patent Application No. 2005/0137648, entitled "System and Method Suitable for Treatment of a Patient with a Neurological Deficit by Sequentially Stimulating Neural Pathways Using a System of Discrete Implantable Medical Devices", which is incorporated herein by reference in its entirety.

In addition or as an alternative to an FES and/or EMG based system, representative types of SSM systems 150 may comprise or be based upon an OxiplexTS™ tissue spectrometer manufactured by ISS, Inc., of Champaign, Ill.; an Imagent™ optical imaging system, also manufactured by ISS, Inc.; or a Geodesic EEG System having a Hydrocel Geodesic Sensor Net® manufactured by Electrical Geodesics, Inc., of Eugene, Oreg.

Figure 4:
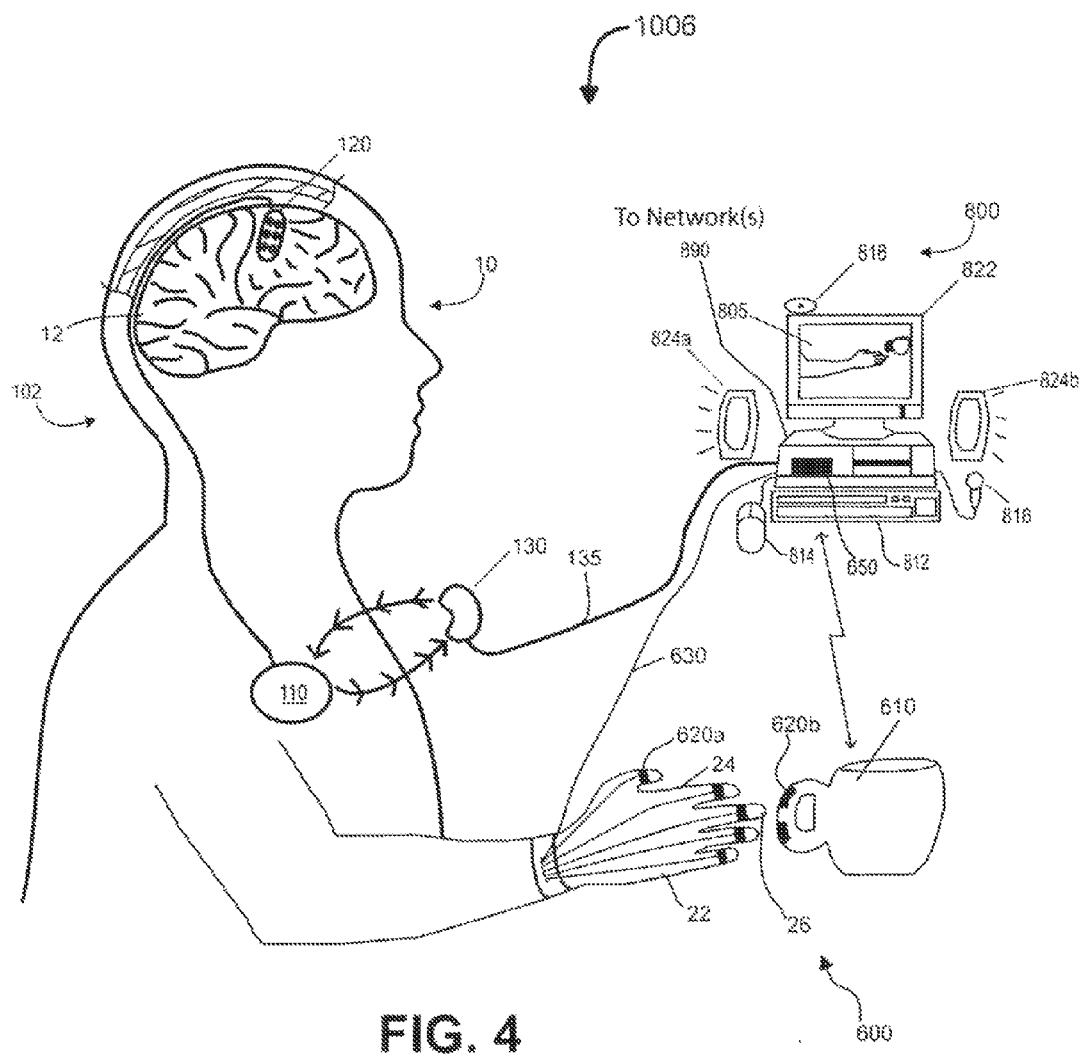
FIG. 4 is a schematic illustration of a PINS system according to yet another embodiment of the invention.

FIG. 4 is a schematic illustration of a PINS system 1006 according to yet another embodiment of the invention. In various embodiments, a PINS system 1006 may comprise an NSS 100; a daily living ART (DL-ART) system, apparatus, or device 600; and a TMC 800. The NSS 100 may comprise one or more types of neural stimulation devices that are identical or analogous to those described above, for example, a set of electrodes or electrode assemblies 120 coupled to an IPG 100; and a communication device 130, which may be configured for communication with the TMC 800 (e.g., by way of a link 135) and/or another programming device (not shown). As further described below, the TMC 800 may comprise a computer system that is configured and adapted to interface with the DL-ART system 600 and possibly the NSS 100.

A DL-ART system 600 may comprise one or more instruments or objects of daily living (ODL) 610 that a patient 10 might encounter, use, manipulate, handle, and/or interact with in a normal daily situation; a set of interaction monitoring elements or devices (IMDs) 620 that facilitate the detection, characterization, and/or analysis of one or more aspects of the patient's interaction with an ODL 610; and a control module 650. The control module 650 may comprise hardware and/or software configured for signal acquisition, processing, and/or analysis, and may be implemented using devices or elements that are separate from and/or carried by or resident within the TMC 800. Referring also again to FIG. 1B, in a representative embodiment, the control module 650 may comprise one or more I/O interfaces or ports 806; a circuit board within the TMC 800 that carries circuit elements (e.g., signal conversion or signal processing circuitry and an electronically readable, configurable, or programmable medium) corresponding to DL-ART system operation; and one or more sets of program instructions associated with or corresponding to the IMDs 620 and/or the ATU 850, PAU 860, and/or SCU 870.

The IMDs 620 may be configured for wireless and/or wire-based communication with each other, the control module 650, and/or the TMC 800. Depending upon embodiment details, one or more IMDs 620 may be carried by the patient 10 and/or an ODL 610 as further described below. Based upon the detection and/or characterization of the patient's interaction with an ODL 610, the TMC 800 may measure, assess, or estimate patient performance relative to particular types of motion, activity, tasks or subtasks at one or more times. The TMC 800 may thereby generate and store baseline and periodic patient performance information.

Based upon signals generated by particular IDMs 610, the TMC 800 may synchronize or approximately synchronize neural stimulation and/or monitoring operations with specific patient actions. In some embodiments the TMC 800 may initiate, query, continue, adjust, interrupt, resume, and/or terminate neural stimulation and/or monitoring operations in an adaptive, essentially adaptive, or generally adaptive manner based upon signals generated by one or more IMDs 610. The TMC 800 may manage adaptive stimulation and/or monitoring operations in a real-time, near-real time, or delayed (e.g., from one behavioral activity attempt to a subsequent attempt, or one therapy period or treatment session to a next) manner. In a manner identical or analogous to that associated with other PINT embodiments described herein, such adaptive neural stimulation may enhance an extent to which an individual experiences neurofunctional development or restoration and/or increase a likelihood that neurofunctional gains are lasting or essentially permanent.

In general, activities of daily living may include putting on or removing clothing; the preparation or consumption of beverages or meals; personal hygiene (e.g., brushing teeth or hair); household cleaning; the use of various types of household devices, appliances, tools, or implements (e.g., a telephone, scissors, or a screwdriver); hobbies (e.g., painting or knitting); and/or a wide variety of other typical behavioral activities. Any given ODL 610 may thus comprise an object or a version of an object that facilitates the performance or attempted performance of particular activities of daily living; and a set of IMDs 620 carried by or mounted upon or within such an object. In certain embodiments, an ODL 610 may also comprise a power source (e.g., a battery or a capacitor) and power management circuitry corresponding to the IMDs 620. As illustrated in FIGS. 4, 5A-5F, and 6, representative types of ODL 610 may correspond to a cup 610a; a food item 610b; a toothbrush 610c; a jar 610d; a writing implement 610e; a button 610f; a pair of scissors 610g; and an iron 610h.

In addition to any IMDs 620 carried by an ODL 610, one or more IMDs 620 may be carried by or mounted upon the patient 10. In the description herein, IMDs 620 carried by the patient 10 are referred to as patient-side IMDs 620a; and IMDs 620 carried by an ODL 610 are referred to as object-side IMDs 620b. In various embodiments, patient-side IMDs 620a may be carried by, mounted upon, and/or incorporated into one or more wearable articles such as a sleeve or glove 622 and/or a set of bands, rings, or clips 624 that surround or reside upon or proximate to portions of a patient's finger tips 26, fingers 24, hand 22, wrist, arm 20, or other body part(s) in a manner indicated in FIG. 4. A wearable article may also carry a power source such as a battery or a capacitor and associated power management circuitry corresponding to one or more patient-side IMDs 610a.

IMDs 620 may facilitate the detection, characterization, and/or analysis of a patient's interaction with an ODL 610 in a wide variety of manners. For example, IMDs 620 may be configured and adapted to generate, output, and/or receive signals that facilitate proximity detection; surface contact sensing; position, orientation, and/or motion detection; force measurement; and/or temperature sensing. Correspondingly, a DL-ART system 600 may be implemented using various types electrical, magnetic, optical, ultrasonic, thermal, mechanical or micromechanical, and/or other technologies.

Figure 6:
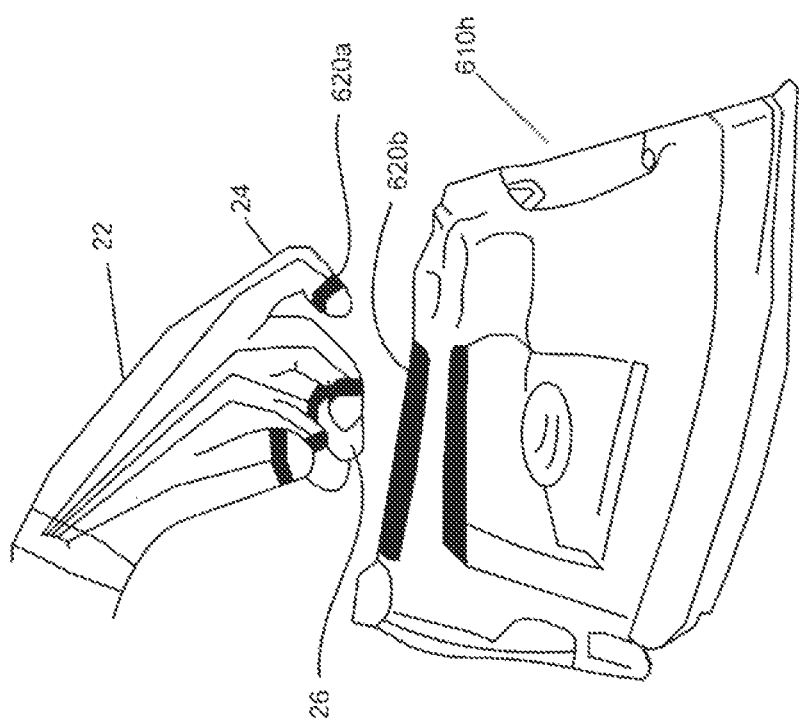
FIG. 6 is a schematic illustration of a patient interacting with an object of daily living in accordance with an embodiment of the invention.

In some embodiments such as those illustrated in FIG. 4 or 6, patient-side IMDs 620a and ODL-side IMDs 620b may be configured for proximity or contact sensing, such that one or more IMDs 620 generate proximity or contact signals in a manner that corresponds to or indicates the presence and/or position(s) of particular patient finger tips 26 proximate to, at, or upon one or more portions of an ODL 610. Depending upon embodiment details, such patient-side and/or ODL-side IMDs 610a-b may comprise a set of electrical signal transfer devices (e.g., conductive surfaces or strips) that affect or establish a signal level in response to circuit completion; RF or ultrasonic emitters, receivers, and/or transceivers; capacitive or field-effect touch sensors (e.g., a sensor comprising or based upon a device manufactured by TouchSensor Technologies of Wheaton, Ill.); and/or other types of devices. In certain embodiments employing one or more touch sensors, such sensors may be carried by the ODL 610 and patient-side IMDs 610b may be omitted, in which case the ODL 610 or its touch sensors 610a may be configured for wireless or wire-based signal communication with the control module 650 and/or the TMC 800 (e.g., as indicated by the dashed line between the ODL 610 and the TMC 800 in FIG. 4).

The control module 650 and/or the TMC 800 may acquire, receive, store, process, and/or analyze proximity or contact signals at one or more times, possibly following the TMC's presentation of particular instructions to the patient 10 (e.g., audio or visual requests to grasp, pick up, hold, manipulate, or release the ODL 610). The TMC 800 may additionally transfer patient performance information comprising or corresponding to proximity or contact signals to a remote location such as a networked computer system or storage device.

In certain embodiments, the TMC 800 may initiate, query, continue, adjust, interrupt, resume, or discontinue neural stimulation and/or monitoring operations based upon 1) proximity or contact signals; and possibly 2) the nature and/or extent of the patient's neurologic dysfunction and general or specific expected, observed, estimated, or measured patient functional limitations (e.g., one or more types of fine motor control) associated with such dysfunction. For example, a patient 10 suffering from hemiparesis may experience significant difficulty performing actions involving finger extension, and comparatively less or little difficulty performing actions involving finger flexion. Thus, after the TMC 800 has instructed the patient 10 to perform an action involving finger extension, such as releasing a cup or appliance handle, the TMC 800 may direct the NSS 100 to apply neural stimulation signals to the patient 10 using a set of stimulation parameters that may facilitate enhanced development of neurofunctional abilities that subserve finger extension.

Based upon one or more proximity or contact signals, the TMC 800 may determine that the patient 10 has grasped an ODL 610, or has extended or begun to extend their fingers 24 to release the ODL 610. The TMC 800 may correspondingly instruct the NSS 100 to apply stimulation signals to the patient 10 in an adaptive or essentially adaptive manner that corresponds to particular patient actions. For instance, the TMC 800 may instruct the NSS 100 to avoid neural stimulation or deliver stimulation signals to the patient 10 in accordance with a first set of stimulation parameters during an activity or time interval associated with reaching or grasping the ODL 610; or initiate neural stimulation or deliver stimulation signals in accordance with a second set of stimulation parameters during an activity or time interval associated with releasing the ODL 610. The second set of stimulation parameters may differ from the first set of stimulation parameters in one or more stimulation sites, signal polarities, peak signal levels, pulse widths, pulse repetition frequencies, interburst or intraburst patterns, signal modulation operations or functions, and/or other parameters.

In a representative example, the first set of stimulation parameters may specify a unipolar or bipolar polarity; a peak current or voltage level that corresponds to 25% of a movement or sensation threshold level or a predetermined maximum stimulation level; a pulse repetition frequency between approximately 35 Hz and 200 Hz (e.g., 50 Hz); and a first phase pulse width between approximately 50 and 300 microseconds (e.g., 100, 200, or 250 microseconds). The second set of stimulation parameters may specify a unipolar polarity; a peak current or voltage level that corresponds to 50% of a movement or sensation threshold level or a predetermined maximum stimulation level; a pulse repetition frequency of 100 Hz; and a first phase pulse width of approximately 250 microseconds. The second set of stimulation parameters may additionally specify parameters that result in the brief application of one or more near-threshold, threshold, and/or suprathreshold pulses or bursts; and/or parameters that correspond to theta burst stimulation or another type of naturally occurring neural discharge behavior. Adapting or varying neural stimulation in one or more of such manners based upon patient activity and/or patient interaction with an object or device may increase a likelihood of providing enhanced and/or long lasting (e.g., for weeks, months, years, or permanently) neurofunctional benefit.

In some embodiments, the IMDs 620 may be implemented using a set of position, orientation, and/or force tracking devices that may generate or communicate corresponding position, orientation, and/or force signals. The TMC 800 may receive, store, and/or analyze such signals, and possibly manage or control neural stimulation and/or monitoring operations in an adaptive or generally adaptive manner in view of such signals.

For example, in certain representative embodiments such as those shown in FIGS. 4 and/or 6, some or each of the IMDs 620 and the control module 650 may comprise or be based upon a motion tracking system, for example, a microBird™, miniBird™, pciBird™, and/or six degree of freedom (DOF) magnetic tracking system manufactured by Ascension Technology Corporation of Burlington, Vt. One or more IMDs 620 or motion tracking devices or elements may be carried by the patient 10 and/or an ODL 610. Such devices can also be positioned or located at a distance from the patient, for example, at particular locations within a room. In a manner analogous to that previously described, in certain embodiments the TMC 800 may adaptively direct neural stimulation and/or monitoring operations in a manner that corresponds to the position, orientation, velocity, stability, and/or forces experienced by particular patient body parts and/or ODLs 610.

Figure 5A:
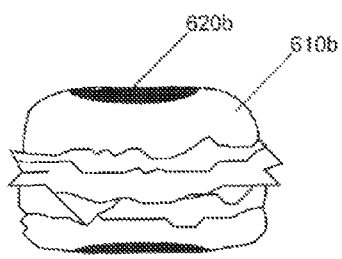
FIGS. 5A-5F are schematic illustrations of representative types of objects of daily living according to an embodiment of the invention.
Figure 5C:
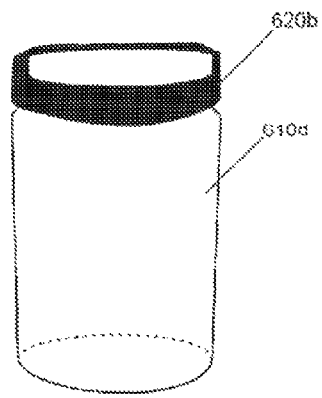
Figure 5B:
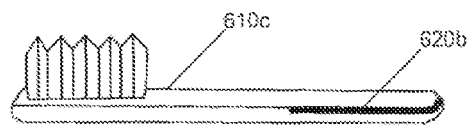
Figure 5D:
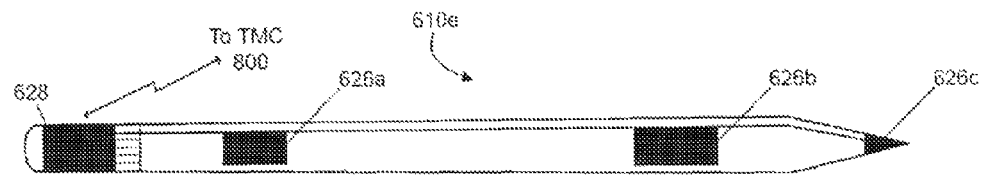
Figure 5E:
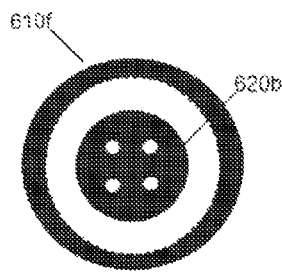
Figure 5F:
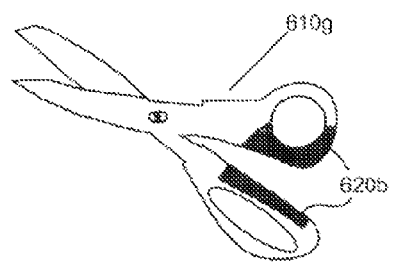

As another example, FIG. 5D is a schematic illustration of an actual or simulated writing implement 610e having a set of IMDs 620b that comprises a set of orientation and/or force sensors 626. The orientation and force sensors 626 may comprise one or more of a level sensor 626a; an accelerometer and/or a gyroscope 626b; and a force or pressure sensor 626c. The orientation and force sensors 626 may be coupled to a transmitter 628 configured to communicate orientation and/or force signals to the control module 650 and/or the TMC 800.

In some embodiments, the writing implement 610e may operate in association with a writing tablet coupled to the TMC 800, in a manner understood by those skilled in the relevant art. The TMC 800 may display example symbols, characters, or pictures upon a display device 822; instruct the patient 10 to create patient-generated symbols, characters, or pictures using the writing implement 610e; receive, store, and/or analyze corresponding orientation and force signals; and display patient-generated symbols, characters, or pictures upon the display device 822. Additionally, based upon the orientation and/or force signals, the TMC 800 may adaptively direct neural stimulation and/or monitoring operations in a manner that corresponds to patient performance in actions relating to writing, such as grasping and/or releasing the writing implement 610e, and/or applying vertical and/or translational forces to the implement 610e.

While not shown in FIGS. 4, 5A through 5F, and 6, particular PINS embodiments 1006 may additionally comprise an SSM system or device 150 that is identical, essentially identical, analogous, or similar to that described above with reference to FIG. 3. Such embodiments may provide particular types of stimulation (e.g., FES) to the patient 10, and/or sense, measure, or monitor patient response and/or patient state signals in one or more manners previously described (e.g., EEG, EMG, hemodynamic, and/or other types of signals). Moreover, certain SSM embodiments may comprise or include one or more implanted microstimulators as described above. In such PINS embodiments 1006, the TMC 800 may direct or oversee neural stimulation and/or monitoring operations in an adaptive or approximately adaptive manner based upon information received from one or more IMDs 610 and/or the SSM.

As indicated above with reference to FIG. 4, in multiple embodiments ODLs 610 may interface with the TMC 800 in a direct or generally direct manner. In addition to items, instruments, or objects of daily living, various other types of devices or elements that may aid an individual's neurofunctional development may interface with the TMC 800 in such a manner, possibly in association with cognitive or memory training, auditory training, visual training, speech or language training, and/or virtual reality games, training, learning, or experiences as described in detail hereafter.

Figure 7:
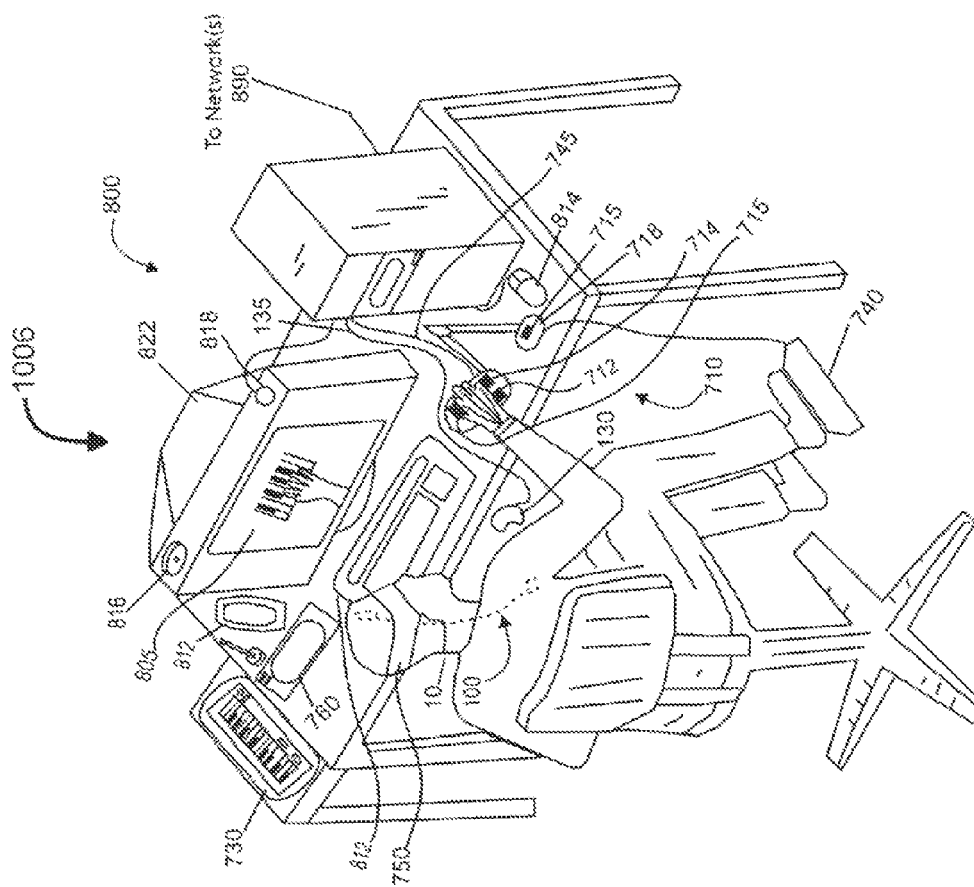
FIG. 7 is an illustration of a PINS system according to another embodiment of the invention.

FIG. 7 is an illustration of a PINS system 1008 according to another embodiment of the invention. In various embodiments, the PINS system 1008 comprises an NSS 100; a TMC 800; one or more virtual ART (V-ART) systems, subsystems, devices, or elements 700 configured to interface with the TMC 800; and possibly an SSM system or device 150 that may also configured to interface with the TMC 800. In several embodiments, such a PINS system 1008 may be implemented using a computer workstation, a desktop computer, a laptop computer, a handheld computer, and/or particular wearable computing or virtual reality devices.

The NSS 100 may comprise one or more neural stimulation devices that are identical, analogous, or similar to those described above. A communication device 130 coupled to the TMC 800 or another programming device may transfer signals to and/or receive signals from the NSS 100. In some embodiments, the TMC 800 may manage or direct neural stimulation and/or monitoring operations, possibly in an adaptive or approximately adaptive manner. In other embodiments, another programming device may manage or direct neural stimulation and/or monitoring operations.

In several embodiments, a V-ART system or device 700 may comprise a set of interactive training tools, devices, structures, and/or elements that provide a given type of user interface in association or conjunction with the TMC 800. Particular portions of such devices, structures, and elements may comprise hardware and/or software, and may reside external to and/or within the TMC 800, in a manner identical or analogous to that for other PINS systems 1000, 1002, 1004, 1006 described above.

Referring also to FIG. 1B, in various embodiments, interactive training tools may include particular types of general-purpose, standardized, and/or frequently encountered user interface or computing devices, such as a keyboard 812, a mouse or trackball 814, a camera 816, a microphone 818, speakers 824, and/or a display or visual presentation device 822.

Additionally or alternatively, interactive training tools may include one or more devices that are configured and adapted for specific types of training, learning, or simulation tasks, such as a haptic system, subsystem, or device 710; a digital glove 720; a musical instrument (e.g., a keyboard) 730; a set of foot pedals 740; a headset 750; and/or a digital writing tablet 760. Those skilled in the art will understand that one or more of a microphone 818, speakers 824, and a visual presentation device 822 may be carried by or incorporated into the headset 750. Interactive training tools may be configured for wire-based or wireless communication with the TMC 800.

The haptic device 710 may comprise a haptic input device 712 and various types of sensors 714 (e.g., force sensor and motion that may detect up to six degrees of freedom) and actuators 715 and/or stimulation devices 716 for providing tactile, proprioceptive, and/or various sensory feedback and/or or forces against the patient's hand and/or arm movements. A digital glove 720 may facilitate the application or delivery of particular types of stimulation, feedback, or forces to the patient 10, and/or monitoring or measurement of forces or patient activity. Such stimulation, feedback, and/or forces may comprise electrical, thermal, or vibratory signals and/or displacements in one or more translational and/or rotational directions. In some embodiments, the haptic input device 712 may be carried or supported by the support structure 718. One or more sensors 714, actuators 715, and/or stimulation devices 716 may be carried by the haptic input device 712 and/or the support structure 718. A detailed description of one type of haptic device 710 that may be suitable for use in particular embodiments of the invention is provided in U.S. Pat. No. 6,714,213, entitled "System and Method for Providing Interactive Haptic Collision Detection", incorporated herein by reference in its entirety.

A detailed description of another type of haptic system or device 710 that may be suitable use in several embodiments of the invention is provided by Priyamvada Tripathi, Kanav Kahol, Leslie C. Baxter et al., in "Rehabilitation of patients with hemispatial neglect using visual-haptic feedback in virtual reality environment," *International Conference on Human-Computer Interaction*, HCII 2005, incorporated herein by reference in its entirety. A PINS system 1008 that includes such a haptic system or device 710 may apply neural stimulation in one or more manners to particular target neural populations in a patient's brain before, during, and/or after the patient 10 performs or attempts to perform multimodal virtual reality haptic rehabilitation activities (e.g., cancellation, tracking, and/or assembling tasks and/or other activities) directed toward restoring neural function that has been affected or lost as a result of a neglect disorder. Such a PINS system 1008 may include one or more types of motion tracking systems, in a manner analogous to that described above.

Referring also to FIG. 1B, the ATU 850 and/or the PAU 860 may manage the presentation of auditory, visual, and/or other information to the patient 10 to facilitate various types of rehabilitation and/or training task or activities. In some embodiments, the ATU 850 and/or the PAU 860 may include a set of program instructions directed toward interpreting or processing haptic device input, and/or selecting or providing given types of haptic stimulation or feedback to the patient 10. Based upon the patient's interaction with the haptic device 710, the ATU 850 may adaptively select or adjust particular types of training or task scenarios presented to the patient 10. Moreover, in certain embodiments, the SAU 870 may exchange signals with the communication device 130 to adaptively adjust neural stimulation and/or monitoring operations based upon patient performance or patient interaction with the haptic device 710. Adjustment of patient training or task scenarios and/or neural stimulation or monitoring operations may occur on a real time or near-real time basis, or on a time delayed basis (e.g., from one training session or therapy period to another).

A musical instrument 730 may comprise a keyboard or synthesizer, a set of electronic drums, and/or other types of actual or mock-up instruments. A musical instrument 730 such as a musical keyboard may also comprise one or more foot pedals 740. Particular musical instruments 730 may support, operate, and/or generate digital information in accordance with a Musical Instrument Digital Interface (MIDI) and/or other format.

Relative to elements illustrated in FIG. 1B, the ATU 850 may manage the generation and presentation of an interactive musical interface to the patient 10. The musical interactive interface may present instructional images, videos, and/or sounds to the patient 10 (e.g., to instruct the patient 10 to play certain musical notes, chords, or sequences); and possibly relayed, captured, or recorded images 805, videos, and/or sounds corresponding to real time, near-real time, or prior patient use of a musical instrument 730. Sounds may be presented by the musical instrument 730 and/or the speakers 824, which may be implemented using headphones or the headset 750.

The ATU 850, possibly in association with the PAU 860, may test, score, and/or evaluate the patient's functionality (e.g., in relation to fine motor skills, memory, cognition, or awareness) or progress at one or more times, and store or transfer such information for subsequent review (e.g., by a clinician). Tests of patient functionality may be directed toward determining patient proficiency in tasks, patterns, or sequences that the patient 10 has already practiced, and/or tasks that are new or unfamiliar to the patient 10 to facilitate the evaluation of one or more aspects of the patient's neurofunctional condition. Based upon patient performance, the ATU 850 may select or adjust particular types of tasks or activities, and/or the SAU 870 may adjust neural stimulation and/or monitoring operations in a manner identical or analogous to that described above.

In several embodiments, standard types of computing devices such as a keyboard 812, a selection device such as a mouse or trackball 814, a microphone 818, a display device 822, and/or speakers 824 may serve as interactive training tools. In such embodiments, the ATU 850 may direct the presentation of various types of textual, auditory, and/or visual information (e.g., images, scenes or scene sequences, or videos) to the patient 10 to facilitate particular types of training or rehabilitation activities. Such training may be directed toward, for example, typing skills, language skills, visual training, memory training, and/or other activities that facilitate neurofunctional development and/or assessment.

In a representative example, the ATU 850 may manage the presentation of a video game to the patient 10. In another representative example, the ATU 850 may direct the presentation of one or more memory or intelligence tests; and/or textual information and a corresponding comprehension test to the patient 10. In another representative example, the ATU 850 may present a patient 10 suffering from symptoms associated with stroke, TBI, or Alzheimer's disease with scenes, scene sequences, and/or video images corresponding to an environment with which the patient 10 may have at least some familiarity. Such scenes or video images may comprise, for example, portions of prerecorded videos of the patient's home and various neighborhood landmarks, and simple navigation paths between such locations. The ATU 850 may instruct the patient 10 to travel to particular destinations by selecting particular travel directions using arrow keys on the keyboard 812 or mouse movement, and update scenes or scene sequences as the patient 10 virtually navigates their neighborhood. The PAU 860 may correspondingly process or evaluate patient performance.

The NSS 100 may apply or deliver one or more forms of neural stimulation to the patient before, during, and/or after the patient 10 interacts with the PINS system 1008. Based upon patient input received from an input device 810 such as the keyboard 812 or mouse 812, the ATU 850 and/or the PAU 850 may select, adjust, or update the presentation of information to the patient 10. Furthermore, in certain embodiments the SAU 870 may adjust neural stimulation and/or monitoring operations during the presentation of such information to the patient 10 in a manner that may correspond to received, processed, and/or analyzed input device signals.

As indicated above, various embodiments of the PINS system 1008 may include an SSM system or device 150 configured for stimulation and/or monitoring operations in one or more manners identical or analogous to those described above. For example, an SSM device 150 may include a set of monitoring devices such as a heart rate monitor, EEG electrode, or blood oxygenation sensor that are worn by the patient or carried by an interactive training tool such as a headset 760. The ATU 850 and/or the PAU 860 may process and/or evaluate signals received from such monitoring devices, and may possibly present such signals to the patient in a manner that facilitates biofeedback training. In some embodiments, the SAU 870 may adjust neural stimulation and/or monitoring operations based upon SSM device signals.

In addition to the foregoing, other types of PINT systems and/or methods directed toward virtual reality training or therapy may be comprise various types of wireless and/or wire-based systems, subsystems, devices, and/or elements configured to generate an immersive virtual reality environment. Such systems or devices may comprise a fully immersive six-sided virtual reality theater, in which individuals may move about, possibly while their motions are tracked based upon signals received from devices the individuals carry or wear. An integrated virtual reality environment that may be suitable for particular PINT embodiments is described in detail by Galen Faidley et al., in "Developing an Integrated Wireless System for Fully Immersive Virtual Reality Environments," (*Proceedings of the Eighth International Symposium on Wearable Computers*, ISWC 2004).

Figure 8:
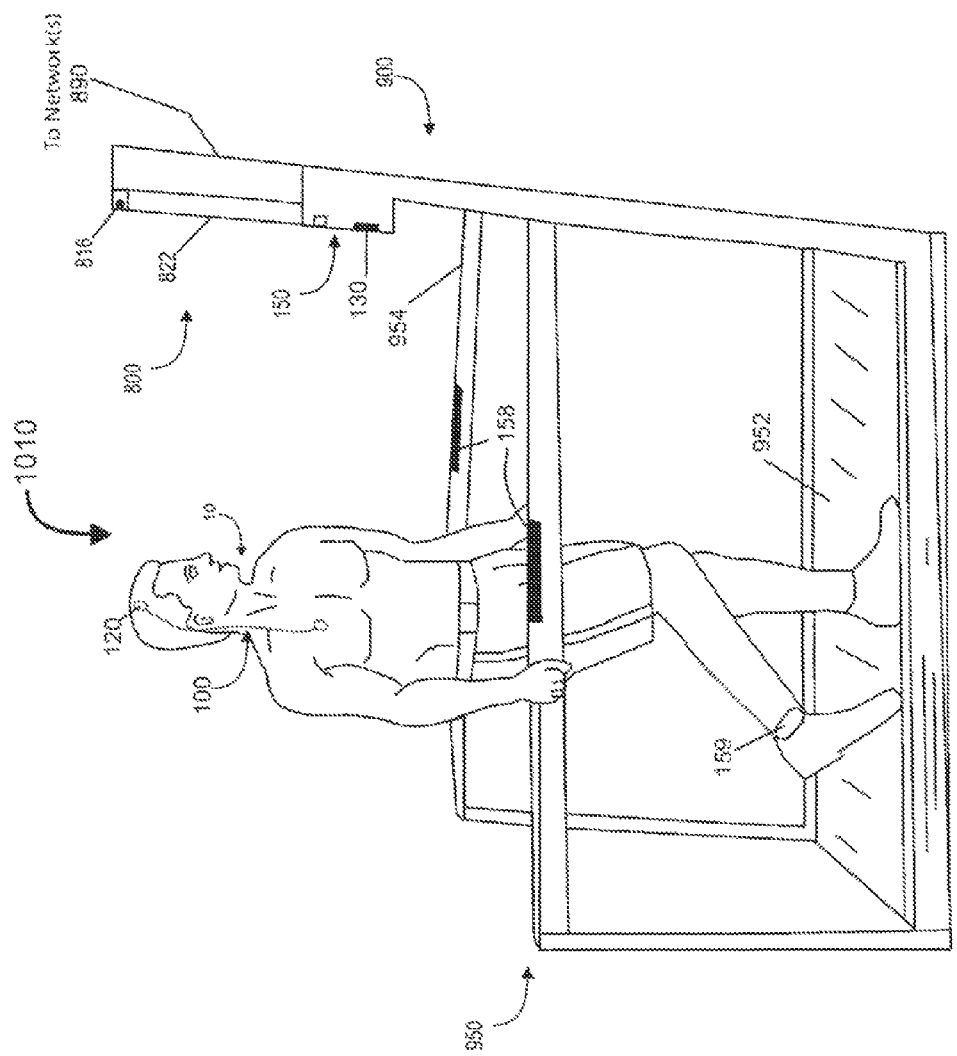
FIG. 8 is a schematic illustration of a PINS system according to another embodiment of the invention.

As an alternative or in addition to various embodiments described above, particular PINT systems may be adapted and configured for the rehabilitation or development of lower extremity function. FIG. 8 is a schematic illustration of another embodiment of a PINS system 1100 in accordance with the present invention. In one embodiment, the PINS system 1100 comprises an NSS 100, a TMC 800, and a lower extremity ART (LE-ART) device 900. The system 1100 may also comprise an SSM device 150, as further described below.

The NSS 100 may comprise one or more types of neural stimulation devices described above, and may receive signals from and/or transfer signals to a communication device 130 that may be coupled to the TMC 800 or another programming device. In a manner identical or analogous to that described above, in certain embodiments the TMC 800 may affect or direct neural stimulation and/or monitoring operations, possibly in an adaptive or patient performance responsive manner.

The LE-ART device 900 may comprise a lower limb motion (LLM) apparatus 950 which may be configured to engage a patient 10 in particular types of lower extremity motion or movement patterns. A treadmill type mechanism is illustrated in the instant embodiment; however, it is to be appreciated that in various embodiments, other configurations may be employed such as a stair climbing apparatus, a stationary bicycle, a simulated skiing apparatus, a trampoline-type apparatus, and/or another type of device. In a treadmill type configuration as illustrated, the LLM apparatus 950 may initiate or adjust the operation of a movement platform 952 in response to patient motion or pressure. The LLM apparatus 950 may include a set of arm rails 954 to provide support to the patient 10 as needed.

In certain embodiments, one or more portions of the TMC 800 may be carried by or mounted upon the LE-ART device 900. For example, a display device 822 may be mounted upon the LLM apparatus 950 in a manner that readily facilitates patient viewing of instructions or information (e.g., a simulated scene and/or a display of signals corresponding to patient activity such as estimated distance traveled) while the patient walks or attempts to walk. Additionally, one or more other portions of the TMC 800 may be carried by the LE-ART device 900, such as a housing in which various TMC hardware and/or software resides, and/or a communication device 130. In an alternate embodiment, the communication device 130 may be carried by a sleeve, cuff, collar, harness, or other patient wearable item.

An SSM system or device 150 in such a PINS embodiment 1100 may comprise one or more gait sensors 158 and/or patient state sensors 159. The gait sensors 158 may be carried by, mounted upon, or worn by the patient 10, and may comprise, for example, a set of accelerometers, gyroscopes, and/or other elements. In a representative embodiment, a gait sensor 158 may comprise or be base upon an activity sensor described by Emil Jovanov et al., in "A wireless body area network of intelligent motion sensors for computer assisted physical rehabilitation," *Journal of NeuroEngineering and Rehabilitation*, 2005, 2:6. An SSM system 150 may itself comprise or interface with a body area network that includes one or more wireless devices that are mounted upon the patient 10.

Patient state sensors 158 may comprise devices configured to sense patient heart rate, temperature, blood flow, blood oxygenation or chemical composition characteristics, and/or other patient related parameters. Patient state sensors 159 may be carried by or mounted upon the patient 10 or the LE-ART device 900 (e.g., on an arm rail 954).

The LE-ART device 900 and the SSM device 150 may generate and transfer signals corresponding to patient performance and state to the TMC 800. The ATU 850 and/or the PAU 860 may process, analyze, characterize, store, and/or transfer (e.g., to a remote clinician system) such signals. Signals or information associated with the LE-ART device 900 and/or the SSM device 150 may provide clinicians or physicians with valuable gait, posture, and overall movement data regarding a patient's neurofunctional state or development.

The ATU 850 and/or the PAU 860 may select or adjust particular types of lower extremity activities based upon patient state signals or patient performance information. Additionally or alternatively, the SAU 870 may adjust or affect neural stimulation and/or monitoring operations based upon patient state signals and/or patient performance information.

Figure 9:
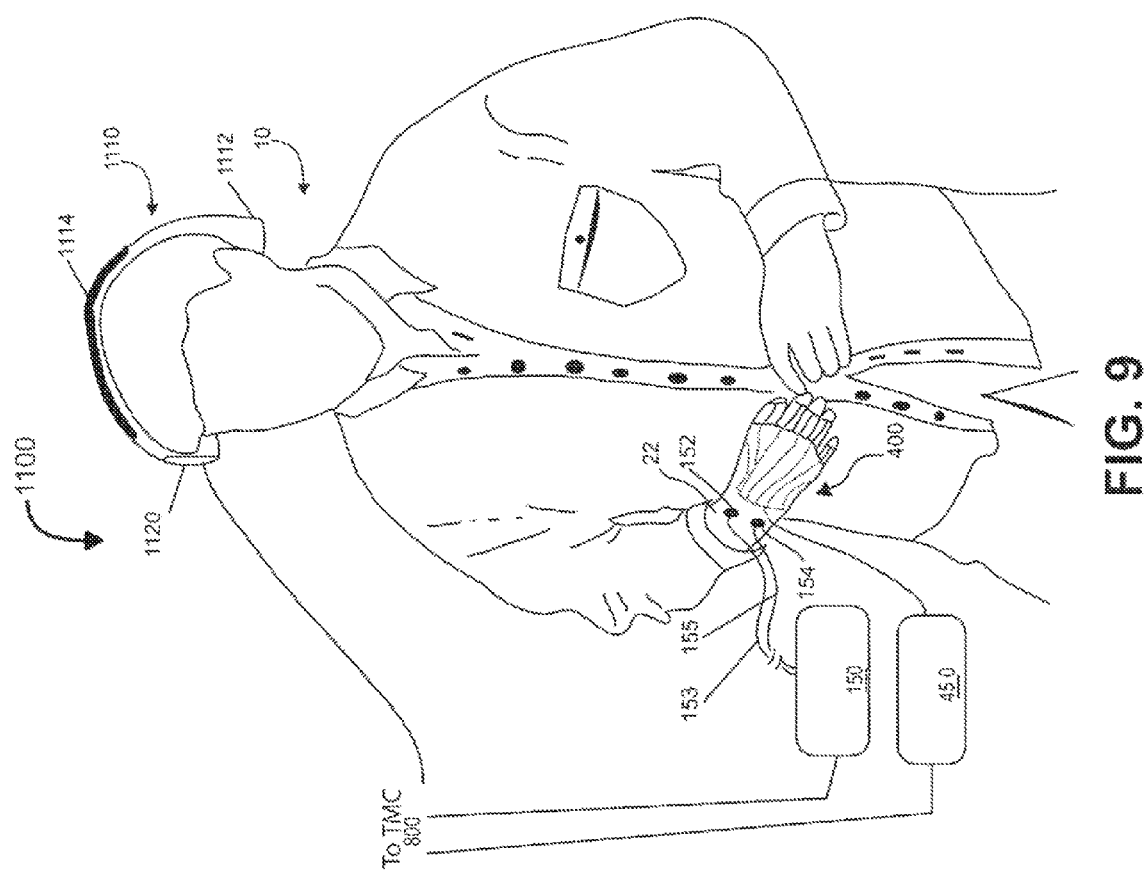
FIG. 9 is a schematic illustration of a PINS system directed toward providing transcranial neural stimulation in accordance with an embodiment of the invention.

As indicated above, various embodiments of the present invention may comprise different types of neural stimulation systems, devices, and/or elements. FIG. 9 is a schematic illustration of a PINS system 1100 directed toward providing transcranial neural stimulation in accordance with an embodiment of the invention. In various embodiments, a PINS system 1100 may comprise a transcranial stimulation system (TSS) 1110; a TMC 800; and possibly an AC-ART device 400 and/or an SSM system or device 150. The TSS 1110 may comprise, for example, a TMS system and/or a tDCS system. In particular embodiments, the TMC 800 may be configured for signal communication with the TSS 1110, the AC-ART device 400, and/or the SSM device 150 at one or more times.

The AC-ART device 400 may comprise one or more types of elements or devices identical or analogous to those described above with reference to FIG. 2, including a controller 450 for controlling various the AC-ART device functions. The controller may be coupled to the TMC 800 by a link 452. Furthermore, the SSM device 150 may comprise one or more types of elements identical or analogous to those previously described, which may be coupled to the TMC 800 by another link 155. In certain embodiments in which an AC-ART device 400 lacks FES capabilities, the SSM device 150 may provide such capabilities.

The TSS 1110 may comprise one or more types of signal generation, transfer, and/or application devices or elements configured to deliver stimulation signals transcranially; a control module 1120 for directing the generation and delivery of such signals; and a power source, power delivery circuitry, and/or power management circuitry. The TSS 1110 may further comprise a structure that may be worn about or proximate to one or more areas selected for neural stimulation, and which carries the control module 1120, the associated signal generation and application elements, and the power related elements.

In some embodiments employing transcranial magnetic stimulation (TMS), a housing 1112 may be configured as a helmet that carries one or more magnetic coils 1114, the control module 1120, and possibly a power source and associated circuitry. The magnetic coils 1114 may be positioned at or relative to one or more stimulation sites, such that magnetic stimulation pulses may be applied to particular cortical and/or subcortical target neural populations or neural structures. The control module 1120 may direct the generation of magnetic pulses in accordance with various stimulation signal parameters, such as peak magnetic field intensity, pulse repetition frequency, and a pulse sequence duration or pulse count. In a representative embodiment, the TSS 110 may comprise or be based upon a helmet-type TMS system as described in U.S. Pat. No. 6,402,678, entitled "Means and Method for the Treatment of Migraine Headaches," incorporated herein by reference in its entirety.

In a manner that is identical, essentially identical, or analogous to that described above, the TSS 1110 may apply or deliver stimulation signals to the patient 10 before, during, and/or after the TMC 800 presents the patient 10 with auditory and/or visual information corresponding to particular types of tasks or activities. The TSS control module 1120 may be configured for wireless or wire-based communication with the TMC 800, for example, by way of a link 1125. Such communication may involve the transfer of configuration data, stimulation parameters, power signals, and/or other signals.

The AC-ART device 400 may comprise an assistive clothing article configured for wearing on a patient body part at a location that is relevant to one or more types of neurofunctional activity or development under consideration. The AC-ART device 400 may be structurally and/or functionally identical, essentially identical, or analogous to that described above with reference to FIG. 2. In some embodiments, the TSS control module 1120 may be coupled to the AC-ART device 400 and/or the SSM device 150, such that the TSS 1110 may apply transcranial stimulation signals to the patient 10 in a manner that is timed or synchronized relative to AC-ART and/or SSM device operation.

The TSS 1110, the AC-ART device 400, and/or the SSM device 150 may transfer signals to the TMC 800. In response, the TMC 800 may process, analyze, or characterize such signals and generate corresponding patient performance data or information. Additionally, the TMC 800 may store or transfer patient performance information to a remote computer system.

The TMC 800 may select and/or adjust particular types of tasks or therapeutic activities based upon received signals and/or patient performance information, in a real-time, near-real time, or delayed manner. Additionally, in one or more manners describe above, in certain embodiments the TMC 800 may initiate, query, modify, interrupt, resume, continue, or terminate operation of the TSS 1110, possibly based upon a type of patient task or rehabilitative training under consideration and/or signals associated with patient performance.

In a representative embodiment wherein an assisted clothing article is adapted to be worn on a hand 22, as shown, patient training may be directed toward performing tasks while manipulating and/or using the hand 22. One example of such a task may involve the patient simulating an ADL like buttoning a shirt. The TSS 1110 may apply one or more types of stimulation signals before, during, and/or after the patient 10 performs or attempts to perform the task. The AC-ART device 400 and/or the SSM device 150 may provide assistive peripheral stimulation in a manner previously described. For instance, while the patient 10 is engaging in a shirt buttoning activity, transcranial stimulation pulses may be delivered by TSS 1110, and functional electrical stimulation pulses may be delivered directly to the hand 22 while the AC-ART device 400 possibly provides mechanized movement assistance for the hand 22. In other embodiments, the TSS 110, the AC-ART device 400, and/or the SSM device 150 may be operate sequentially or individually during task performance, or in various combinations relative to the performance of single or multiple task attempts or repetitions to enhance a likelihood of achieving a desired therapeutic effect.

Representative PINS-ACT System Embodiments

As indicated above, neural stimulation may be combined with multiple types of adjunctive therapy, which may include behavioral therapies and/or chemical substance therapies. One or more chemical substance therapies may be applied or delivered to a patient 10 simultaneously with or separately from neural stimulation and/or behavioral therapy. Moreover, one or both of neural stimulation signal and chemical substance delivery may be controlled or modified in an adaptive manner, either separately, concurrently, or somewhat concurrently.

Figure 10:
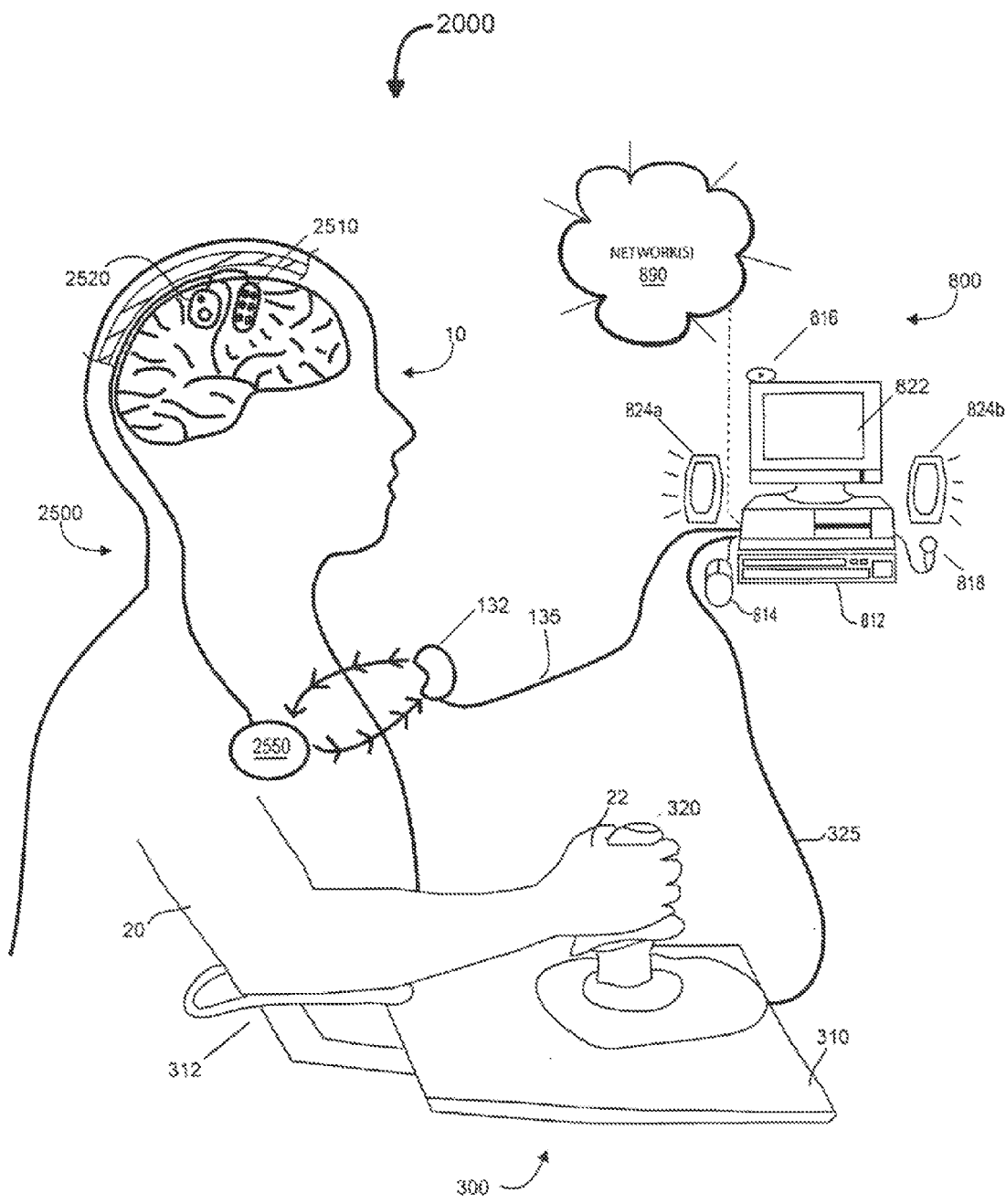
FIG. 10A is a schematic illustration of a PINS-adjunctive chemical therapy system according to an embodiment of the invention.
FIG. 10B is a block diagram of a TMC according to another embodiment of the invention.

FIG. 10A is a schematic illustration of a PINS-ACT system 2000 according to an embodiment of the invention. Relative to FIGS. 1A and 1B, like reference numbers indicate like or analogous elements. In one embodiment, the PINS-ACT system comprises a neural stimulation and chemical delivery (NSCD) system 2500; one or more types of ART devices, such as essentially any ART device previously described; and a TMC 800.

The NSCD system 2500 may comprise a set of neural stimulation devices or elements 2510 and a set of substance delivery devices or elements 2520 coupled to a control module 2550. The neural stimulation elements 2510 may comprise one or more electrode devices and/or signal transfer elements, in a manner identical or analogous to that described above. Depending upon embodiment details, the substance delivery elements 2520 may comprise one or more of a chemical source or reservoir, a fluid or substance transfer element (e.g., a catheter and/or a port), and a substance application mechanism. The NSCD system 2500 may further comprise one or more monitoring devices for sensing, detecting, and/or measuring signals and/or substances (e.g., chemical levels and/or biological markers) associated with neural stimulation, chemical substance delivery, and/or patient state.

Neural stimulation elements 2510 may be positioned or implanted relative to a set of neural stimulation sites, and substance delivery elements 2520 may be positioned relative to a set of substance application sites. A substance application site may correspond to an anatomical location that is essentially identical to, near, or different from a neural stimulation site.

The control module 2550 may comprise an implantable housing that carries control circuitry for directing the operation of the neural stimulation elements 2510 and chemical delivery elements 2520; communication circuitry; and power circuitry. The control module 2550 may be configured for wireless signal transfer with a communication device 132, which may be coupled to a TMC 800 and/or another type of programming device.

Figure 10B:
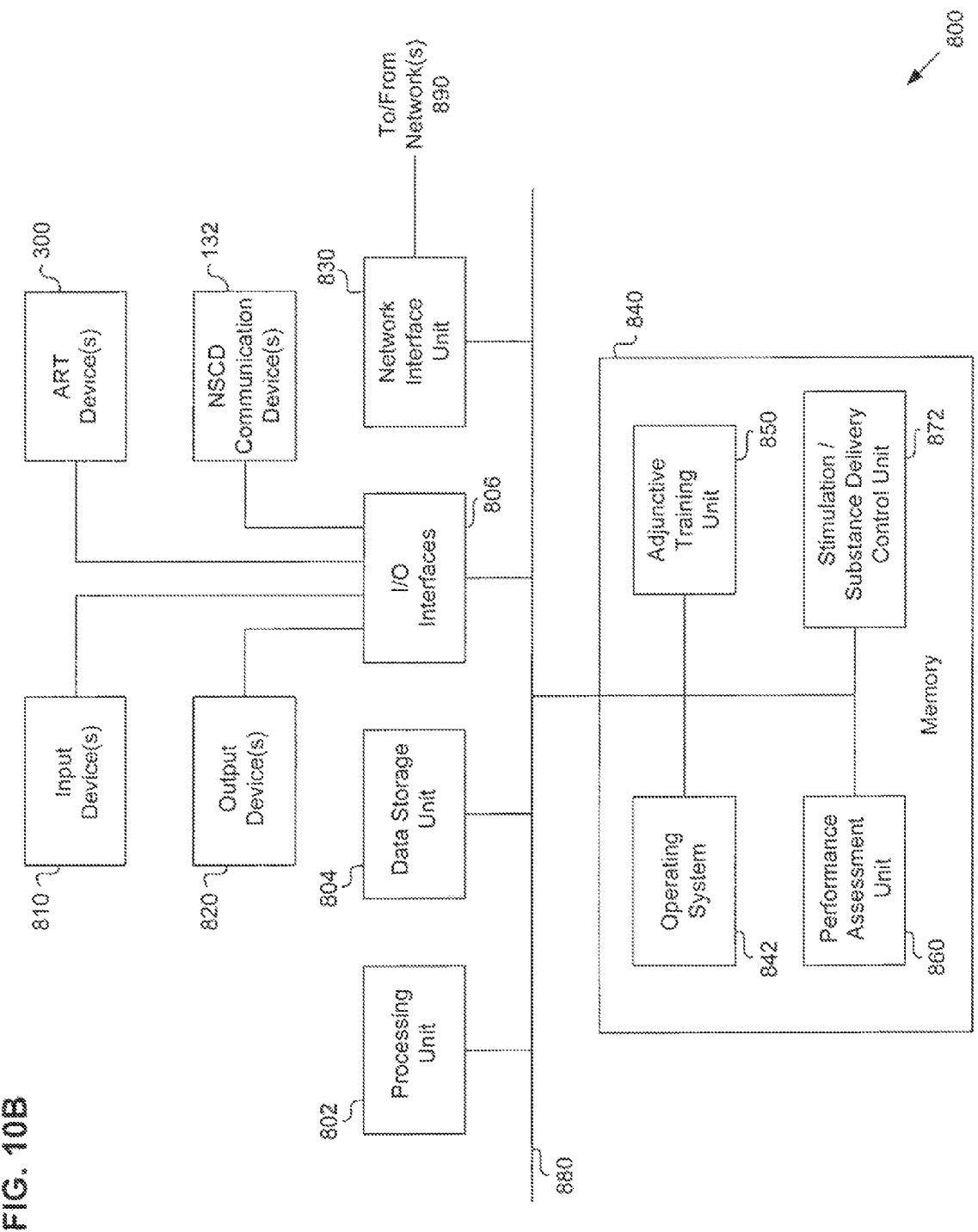

FIG. 10B is a block diagram of a TMC 800 according to an embodiment of the invention. Relative to FIG. 1B, like reference numbers indicate like or analogous elements. The TMC 800 and/or the ART device may operate in one or more manners previously described to engage the patient in particular types of activities directed toward restoring or enhancing neural function. The TMC 800 and/or the ART device may capture, acquire, receive, process, and/or analyze signals corresponding to patient performance and/or patient state. In certain embodiments, the TMC 800 and/or an ART device may direct the NSCD system 2500 (FIG. 10A) to initiate, query, adjust, interrupt, resume, continue, and/or terminate neural stimulation and/or chemical substance delivery operations based upon such signals. Such direction may occur on a real time, non-real time, or delayed basis, in one or more manners previously described. Depending upon embodiment details, neural stimulation parameters may remain unchanged while substance delivery parameters are updated or modified; substance delivery parameters may remain unchanged while neural stimulation parameters are modified; or both neural stimulation and substance delivery parameters may be modified, possibly in an interrelated and/or simultaneous manner.

While the PINS-ACT system 2000 is shown in FIG. 10A in relation to an embodiment that is analogous to the PINS system 1000 shown in FIG. 1A, an NSCD system 2500 may be employed in essentially any type system described above with reference to FIGS. 1A through 9.

Representative PICT System Embodiments

In certain embodiments of the invention, one or more chemical substances may be applied to a patient 10 in lieu of neural stimulation. In association with a chemical substance therapy, the patient 10 may perform one or more types of behavioral activities that may be relevant to restoring or enhancing neural function.

Figure 11:
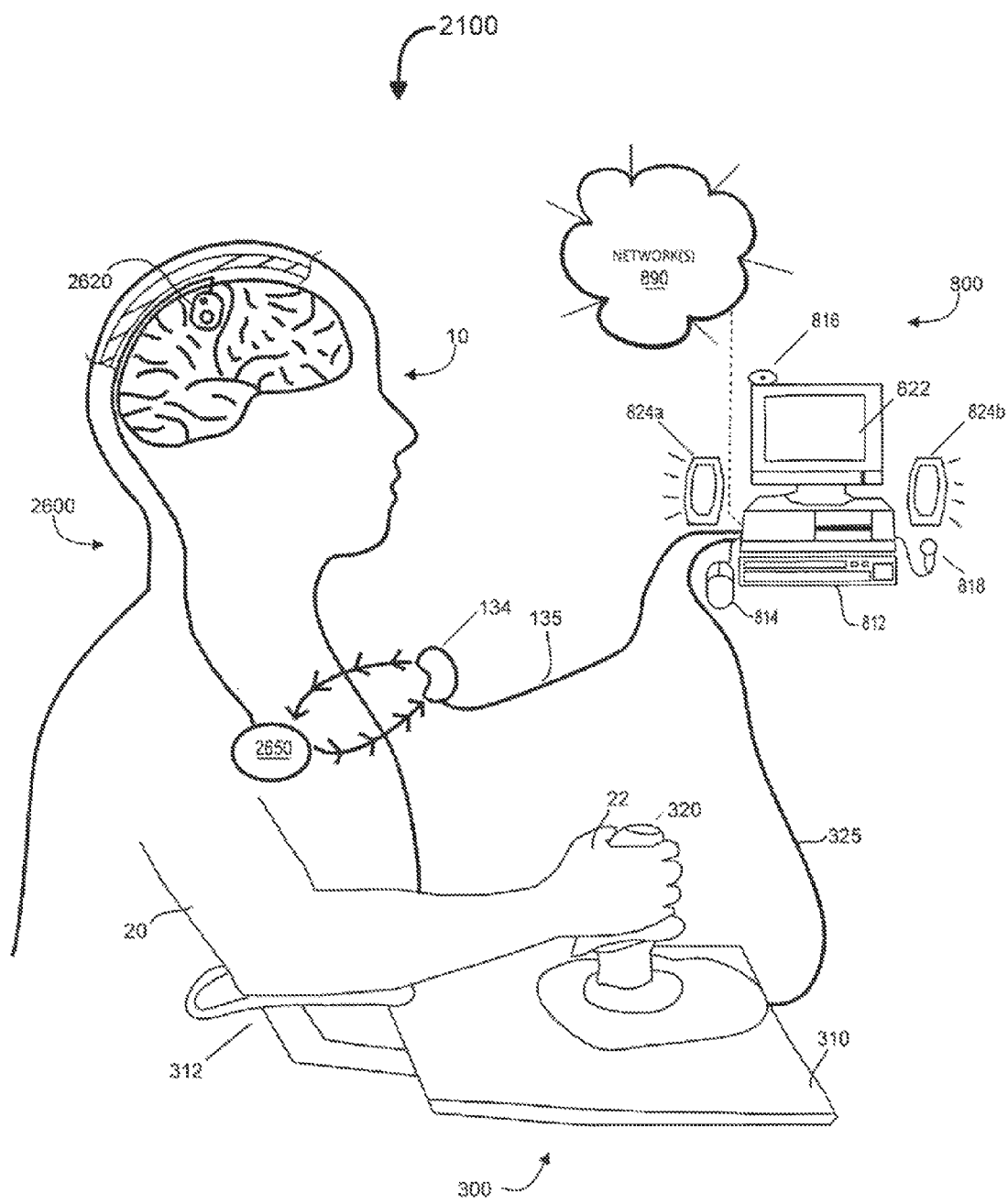
FIG. 11A is a schematic illustration of a patient interactive chemical therapy system according to an embodiment of the invention.
FIG. 11B is a block diagram of a TMC according to another embodiment of the invention.

FIG. 11A is a schematic illustration of a PICT system 2100 according to an embodiment of the invention. Relative to previously described Figures, like reference numbers indicate like or analogous elements. In one embodiment, a PICT system 2100 comprises a substance delivery system (SDS) 2600; one or more types of ART devices, such as essentially any ART device previously described; and a TMC 800.

The SDS 2600 may comprise an implantable drug pump or other device configured to dispense, release, or deliver one or more chemical substances. In one embodiment, the SDS 2600 comprises a set of substance delivery elements 2620 coupled to a control module 2650. The SDS 2600 may further comprise one or more monitoring devices, in a manner analogous to that described above. The SDS 2600 may be configured for wireless signal transfer with a communication device 134, which may be coupled to the TMC 800 or another programming device.

Figure 11B:
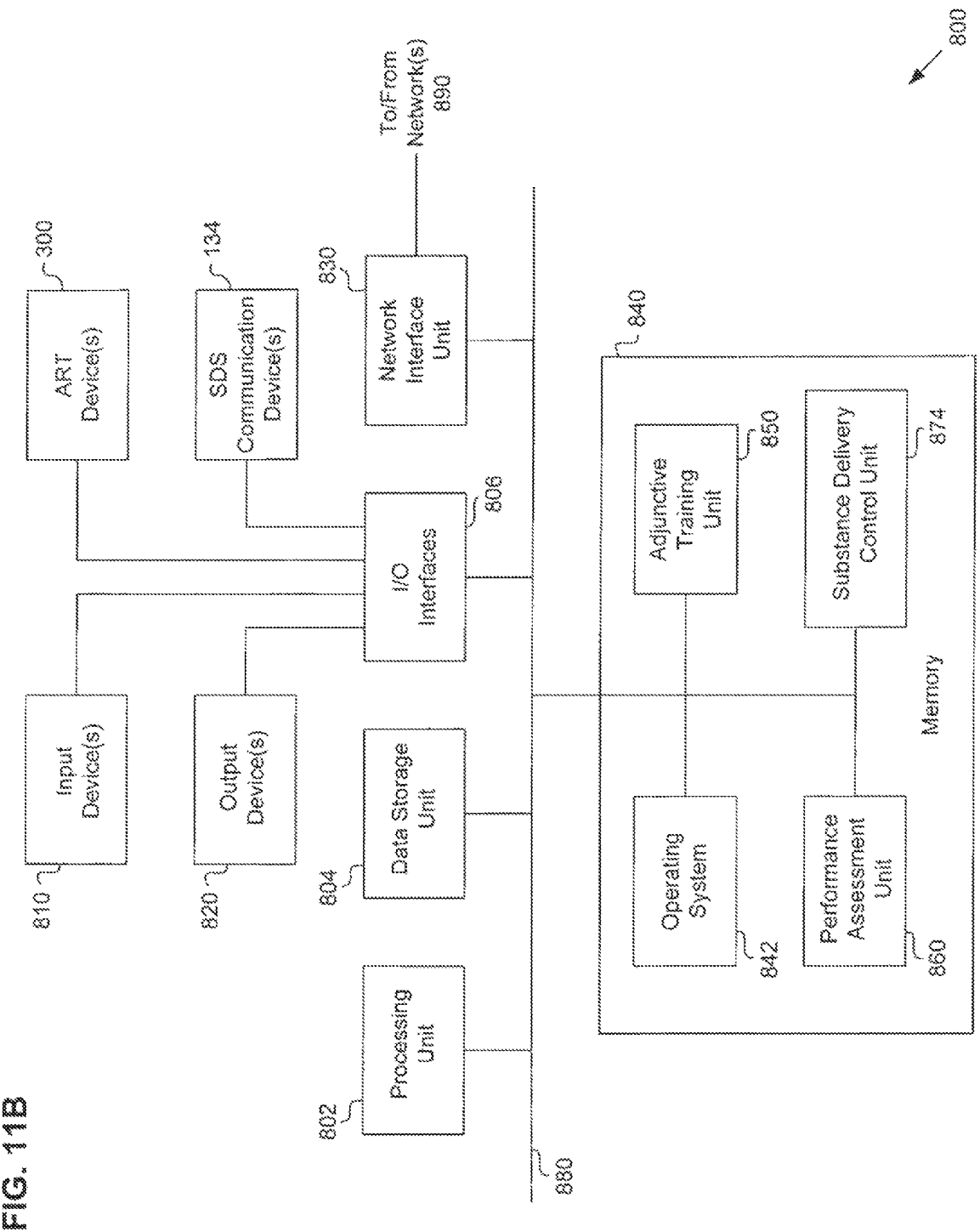

FIG. 11B is a block diagram of a TMC 800 according to an embodiment of the invention. Relative to FIG. 1B, like reference numbers indicate like or analogous elements. The TMC 800 and/or the ART device may operate in one or more manners previously described to engage the patient in particular types of activities directed toward restoring or enhancing neural function. The TMC 800 and/or the ART device may capture, acquire, receive, process, and/or analyze signals corresponding to patient performance and/or patient state. In certain embodiments, the TMC 800 and/or an ART device may direct the SDS 2600 to initiate, query, adjust, interrupt, resume, continue, and/or terminate chemical substance delivery operations based upon such signals. Such direction may occur on a real time, non-real time, or delayed basis, in one or more manners previously described.

While the PNCT system 2100 is shown in FIG. 11A in relation to an embodiment that is analogous to the PINS system 1000 shown in FIG. 1A, a SDS 2600 may be employed in essentially any type of system described above with reference to FIGS. 1A through 9.

Representative PINT Procedures

Figure 12:
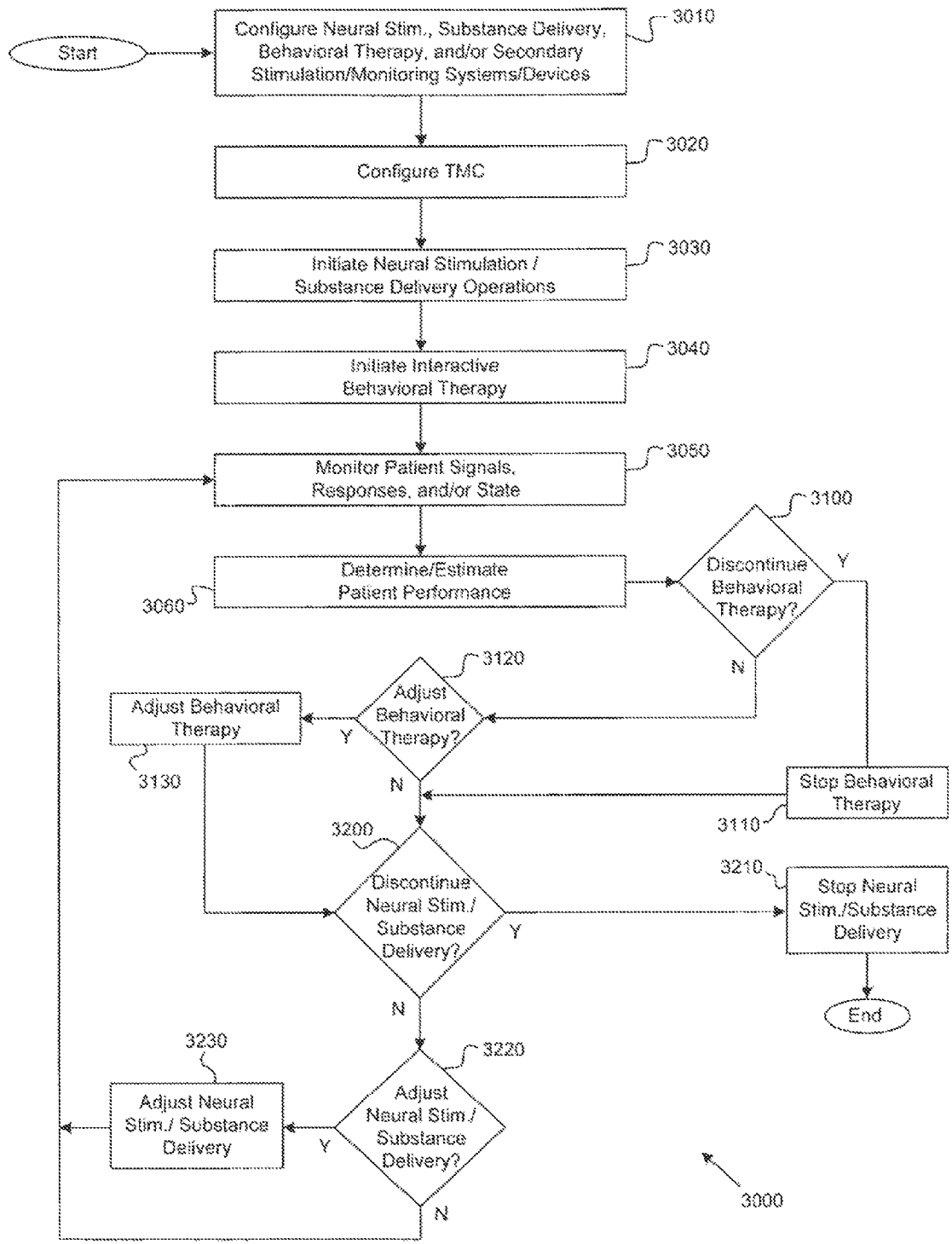
FIG. 12 is a flow diagram illustrating a process for interactive neural stimulation and/or substance delivery according to an embodiment of the invention.

FIG. 12 is a flow diagram illustrating a procedure or process 3000 for interactive neural stimulation and/or substance delivery according to an embodiment of the invention. Process 3000 may comprise various process portions, particular aspects of which are described in detail hereafter.

Process portion 3010 may be directed toward configuring particular neural stimulation and/or substance delivery devices; one or more behavioral therapy systems or devices (e.g., ART devices described above and/or ODLs 610); and/or particular SSM devices for operation. Process portion 3010 can include selecting particular stimulation, substance delivery, and/or monitoring parameters; or selecting or initializing certain behavioral therapy devices, tasks, tests, and/or virtual scenarios. Process portion 3010 can further include positioning or locating a patient 10 for ART device operation. Process portion 3020 is directed toward configuring a TMC for operation, which may include loading and/or initializing particular software for communicating with the ART device, an NSS 100, an NSCD system 2500, and/or a SDS 2600.

Process portion 3030 can include applying neural stimulation signals and/or a chemical substance to the patient 10, and process portion 3040 can include engaging the patient 10 in an interactive therapy, task, activity, test, and/or virtual or simulated environment by way of an ART system or device and/or the TMC 800.

Process portion 3050 can include monitoring various types of patient performance related signals, patient responses, and/or biological signals or markers associated with neural stimulation, chemical substance delivery, and/or patient performance or attempted performance of an interactive activity, in particular manners such as those described above. Process portion 3050 can include processing or analyzing such signals to determine or estimate a level of patient performance, the patient's neurofunctional condition, and/or neurofunctional gains over time.

Process portion 3100 can include determining whether to discontinue or interrupt a behavioral therapy or activity, possibly based upon monitored signals and/or patient performance, or patient completion of an activity. If so, process portion 3110 can include stopping or interrupting the operation of an ART device. In the event that behavioral therapy is to continue, process portion 3120 can include determining whether to adjust a behavioral therapy, task, test, or virtual scenario, possibly based upon monitored signals and/or patient performance information. Process portion 3130 can include adjusting behavioral therapy in one or more manners described above.

Process portion 3200 can include determining whether to discontinue or interrupt neural stimulation and/or chemical substance delivery, possibly based upon monitored signals, patient performance, patient completion of particular tasks, and/or an expiration of a time period or interval. If so, process portion 3210 can include discontinuing or interrupting neural stimulation and/or chemical substance delivery, after which the process 3000 may end.

Process portion 3220 can include determining whether to adjust neural stimulation and/or chemical substance delivery, possibly based upon monitored signals, patient performance, patient completion of particular tasks, and/or an expiration of a time period or interval. If so, process portion 3210 can include adjusting neural stimulation and/or chemical substance delivery in one or more manners described above. During and/or following an adjustment or modification of neural stimulation and/or chemical substance delivery parameters, particular process portions may continue to function in one or more manners previously described.

From the foregoing, it will be appreciated that specific embodiments of the invention have been described herein for purposes of illustration, but that various modifications may be made without deviating from the invention. For example, further embodiments of related systems and methods are disclosed in the following copending patent applications, filed concurrently herewith and incorporated herein by reference: U.S. patent application Ser. No. 11/254,060, titled "Methods and Systems for Improving Neural Functioning, Including Cognitive Functioning and Neglect Disorders"; U.S. patent application Ser. No. 11/737,673, titled "Methods and Systems for Establishing Parameters for Neural Stimulation"; and U.S. patent application Ser. No. 11/583,349, titled "Neural Stimulation and Optical Monitoring Systems and Methods". Aspects of the invention described in the context of particular embodiments may be combined or eliminated in other embodiments. Further, while advantages associated with certain embodiments of the invention have been described in the context of those embodiments, other embodiments may also exhibit such advantages, and not all embodiments need necessarily exhibit such advantages to fall within the scope of the invention. Accordingly, the invention is not limited except as by the appended claims.

We claim:

1. A system for facilitating limb movement in a patient that is suffering from or has suffered a neurological disorder or event; the system comprising:
   a neural stimulation system having an implantable pulse generator that is coupled to at least one electrode assembly capable of delivering electrical pulses to the patient's brain;
   a robotic system configured to facilitate movement of the patient's limb;
   a control system operatively coupled to the robotic system and the neural stimulation system, the control system having a computer-readable medium having instructions, wherein the instructions include:
      automatically receiving information from the robotic system, the information being correlated with the patient's performance of a task using the robotic system; and
      based at least in part on the information received from the robotic system, automatically controlling a parameter in accordance with the neural stimulation system or the robotic system to facilitate limb movement.

2. The system of claim 1 wherein the robotic system comprises at least one robotic element that is positioned to resist patient movement under direction of the control system.

3. The system of claim 1 wherein the robotic system comprises the at least one robotic element that is positioned to assist patient movement under direction of the control system.

4. The system of claim 1 wherein the patient has suffered a stroke.

5. The system of claim 1 wherein the patient is suffering from Parkinson's disease.

6. The system of claim wherein the patient is suffering from hemiparesis, spasticity, neglect, bradykinesia or a combination thereof.

7. The system of claim 1 wherein the electrode assembly is positionable under the skull and over the dura of a cortical target selected from a group consisting of motor cortex, premotor cortex, somatosensory cortex, and prefrontal cortex.

8. The system of claim 1 further comprising a secondary stimulation system.

9. The system of claim 1 wherein the robotic system comprises an element or elements to assist in restoration of hand movement, arm movement or a combination thereof.

10. The system of claim 9 wherein the element comprises at least one arm member, at least one elbow member coupled to the at least one arm member to form rotational axes, a set of actuators configured to facilitate arm member motion, a set of sensors configured to sense and quantify position, force, speed, of arm members or elbow joints, at least one gripping portion configured for grasping, or a combination thereof.

11. The system of claim 1 wherein the robotic system comprises an element or elements to sense, analyze, monitor or a combination thereof the patient's interaction with an object of daily living.

12. The system of claim 11 wherein the element is associated with a wearable item by the patient.

13. The system of claim 12 wherein the wearable item is a glove having the element configured as a set of bands that is proximate to a portion of the patient's fingers, hand, wrist, arm or a combination thereof.

14. The system of claim 12 wherein the wearable item is a sleeve having the element configured as a set of bands that is proximate to a portion of the patient's fingers, hand, wrist, arm or a combination thereof.

* * * * *